US012760007B2

(12) United States Patent
Jiang et al.

(10) Patent No.: US 12,760,007 B2
(45) Date of Patent: Oct. 13, 2026

(54) SALT AND CRYSTAL FORMS OF GLP-1R AGONISTS AND USES THEREOF

(71) Applicant: QILU REGOR THERAPEUTICS INC., Shanghai (CN)

(72) Inventors: Meng Jiang, Suzhou (CN); Beibei Chen, Ningbo (CN); Xudong Wei, Coventry, RI (US); Wenge Zhong, Thousand Oaks, CA (US)

(73) Assignee: QILU REGOR THERAPEUTICS INC., Shanghai (CN)

( * ) Notice: Subject to any disclaimer, the term of this patent is extended or adjusted under 35 U.S.C. 154(b) by 822 days.

(21) Appl. No.: 17/927,502

(22) PCT Filed: May 26, 2021

(86) PCT No.: PCT/US2021/034191

§ 371 (c)(1),
(2) Date: Nov. 23, 2022

(87) PCT Pub. No.: WO2021/242817

PCT Pub. Date: Dec. 2, 2021

(65) Prior Publication Data

US 2023/0203023 A1 Jun. 29, 2023

(30) Foreign Application Priority Data

May 27, 2020 (WO) ................ PCT/CN2020/092530

(51) Int. Cl.
*C07D 405/14* (2006.01)
*C07C 55/22* (2006.01)

(52) U.S. Cl.
CPC ............ *C07D 405/14* (2013.01); *C07C 55/22* (2013.01); *C07B 2200/13* (2013.01)

(58) Field of Classification Search
None
See application file for complete search history.

(56) References Cited

U.S. PATENT DOCUMENTS

2020/0283424 A1 9/2020 Zhong
2022/0024901 A1 1/2022 Zhong
2023/0382899 A1 11/2023 Zhong et al.

FOREIGN PATENT DOCUMENTS

| | | | |
|---|---|---|---|
| CN | 111978313 | A | 11/2020 |
| TW | 201613883 | A | 4/2016 |
| WO | 2002/088093 | A1 | 11/2002 |
| WO | 2007/060408 | A2 | 5/2007 |
| WO | 2007/110868 | A2 | 10/2007 |
| WO | 2008/012623 | A1 | 1/2008 |
| WO | 2011/143365 | A1 | 11/2011 |
| WO | 2013/090454 | A2 | 6/2013 |
| WO | 2014/201172 | A1 | 12/2014 |
| WO | 2018/109607 | A1 | 6/2018 |
| WO | 2020/103815 | A1 | 5/2020 |
| WO | 2020/207474 | A1 | 10/2020 |
| WO | 2021/197464 | A1 | 10/2021 |

OTHER PUBLICATIONS

Roth. British Journal of Pharmacology, 2012, 166, 121-136 (Year: 2012).*
Drucker. Cell Metabolism, 2016, 24, 15-30 (Year: 2016).*
Matalliotakis. Archives of Gynecology and Obstetrics, 2006, 274, 187-197 (Year: 2006).*
International Search Report and Written Opinion for Application No. PCT/CN2020/092530, dated Feb. 25, 2021, 18 pages.
International Search Report and Written Opinion for Application No. PCT/US2021/034191, dated Jul. 27, 2021, 8 pages.
International Search Report and Written Opinion for Application No. PCT/CN2021/123387, dated Jan. 4, 2022, 8 pages.
International Preliminary Report on Patentability for Application No. PCT/CN2021/123387, dated Apr. 27, 2023, 7 pages.
U.S. Appl. No. 18/031,380, filed Apr. 12, 2023, 2023-0382899, Published.

* cited by examiner

*Primary Examiner* — Noble E Jarrell
(74) *Attorney, Agent, or Firm* — McCarter & English, LLP; Yu Lu; Wei Song

(57) ABSTRACT

Various salt forms of Compound I and Compound II represented by the following structural formulae, and their corresponding pharmaceutical compositions, are disclosed. (I), (II) Particular single crystalline forms of 1:1 Compound I tris salt, 1:1 Compound II tris salt, and 1:1 Compound II citrate salt are characterized by a variety of properties and physical measurements. Methods of preparing specific crystalline forms are also disclosed. The present disclosure also provides methods of treating type 2 diabetes mellitus, prediabetes, obesity, non-alcoholic fatty liver disease, non-alcoholic steatohepatitis, and cardiovascular disease in a subject.

Compound I

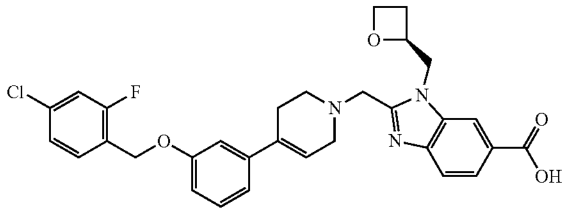

Compound II

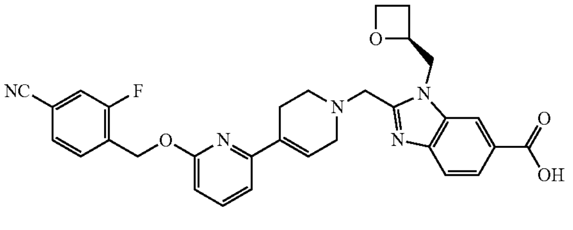

22 Claims, 10 Drawing Sheets

SALT AND CRYSTAL FORMS OF GLP-1R AGONISTS AND USES THEREOF

CROSS REFERENCE TO RELATED APPLICATIONS

This application is a U.S. national stage filing, under 35 U.S.C. § 371(c), of International Patent Application Number PCT/US2021/034191, filed on May 26, 2021, which claims the benefit of priority to International Patent Application Number PCT/CN2020/092530, filed on May 27, 2020. The entire contents of the aforementioned applications are incorporated herein by reference by their entireties.

BACKGROUND

GLP-1 is a 30 amino acid long incretin hormone secreted by the L-cells in the intestine in response to ingestion of food. GLP-1 has been shown to stimulate insulin secretion in a physiological and glucose-dependent manner, decrease glucagon secretion, inhibit gastric emptying, decrease appetite, and stimulate proliferation of beta-cells. In non-clinical experiments GLP-1 promotes continued beta-cell competence by stimulating transcription of genes important for glucose-dependent insulin secretion and by promoting beta-cell neogenesis (Meier et al., *Biodrugs.* 17(2): 93-102, 2013).

In a healthy individual, GLP-1 plays an important role regulating post-prandial blood glucose levels by stimulating glucose-dependent insulin secretion by the pancreas resulting in increased glucose absorption in the periphery. GLP-1 also suppresses glucagon secretion, leading to reduced hepatic glucose output. In addition, GLP-1 delays gastric emptying and slows small bowel motility delaying food absorption. In people with T2DM, the normal post-prandial rise in GLP-1 is absent or reduced (Vilsboll et al., *Diabetes.* 50:609-613, 2001).

Hoist (*Physiol. Rev.* 87:1409, 2007) and Meier (*Nat. Rev. Endocrinol.* 8:728, 2012) describe that GLP-1 receptor agonists, such as GLP-1, liraglutide and exendin-4, have 3 major pharmacological activities to improve glycemic control in patients with T2DM by reducing fasting and post-prandial glucose (FPG and PPG): (i) increased glucose-dependent insulin secretion (improved first- and second-phase), (ii) glucagon suppressing activity under hyperglycemic conditions, (iii) delay of gastric emptying rate resulting in retarded absorption of meal-derived glucose.

International Patent Application No. PCT/CN2019/119373, the entire teachings of which are incorporated herein by reference, discloses highly potent GLP-1 agonists. The structures of two agonists disclosed therein, referred to herein as "Compound I" and "Compound II" are shown below:

Compound I

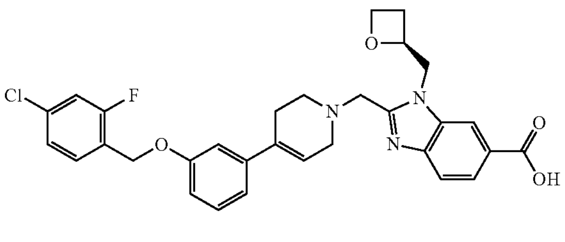

-continued

Compound II

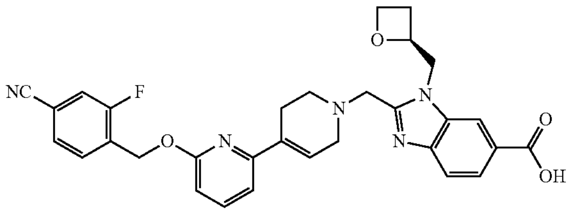

The chemical name of Compound I is (S)-2-((4-(3-((4-chloro-2-fluorobenzyl)-oxy)phenyl)-3,6-dihydropyridin-1 (2H)-yl)methyl)-1-(oxetan-2-ylmethyl)-1H-benzo[d]-imidazole-6-carboxylic acid.

The chemical name of Compound II is (S)-2-((6-((4-cyano-2-fluorobenzyl)oxy)-3',6'-dihydro-[2,4'-bipyridin]-1' (2'H)-yl)methyl)-1-(oxetan-2-ylmethyl)-1H-benzo[d]imidazole-6-carboxylic acid.

The successful development of pharmaceutically active agents, such as Compound I or Compound II, typically requires the identification of a solid form with properties that enable ready isolation and purification following synthesis, that are amendable to large scale manufacture, that can be stored for extended periods of time with minimal absorption of water, decomposition or transformation into other solid forms, that are suitable for formulation and that can be readily absorbed following administration to the subject (e.g., are soluble in water and in gastric fluids).

SUMMARY

It has now also been found that the 1:1 Compound I tris salt, 1:1 Compound II tris salt, and 1:1 Compound II citrate salt can be crystallized under well-defined conditions to provide desired crystalline forms (see Examples 3-7). These three salts also have good solubility in water and in simulated gastric fluids, and solid stability (see Tables 2 and 7-1), have high melting point onsets. 1:1 Compound I tris salt and 1:1 Compound II tris salt are also suitable for large scale synthesis.

The designation "1:1" is the molar ratio between acid (citric acid)/base (tris-(hydroxymethyl)aminomethane) and Compound I/Compound II. Because of the three carboxylic acid groups on citric acid and the two basic nitrogen atoms in Compound II, multiple possible stoichiometries are possible. The 1:1 citric acid salt of Compound (I) is referred to herein as "1:1 Compound II citrate salt."

In one aspect, the present disclosure provides a tris salt of Compound I wherein the molar ratio between Compound I and tris-(hydroxymethyl)aminomethane is 1:1. As noted above, this salt is also referred to herein as "1:1 Compound I tris salt".

In another aspect, the present disclosure provides a tris salt of Compound II wherein the molar ratio between Compound II and tris-(hydroxymethyl)aminomethane is 1:1. As noted above, this salt is also referred to herein as "1:1 Compound II tris salt".

In another aspect, the present disclosure provides a citrate salt of Compound II wherein the molar ratio between Compound II and citric acid is 1:1. As noted above, this salt is also referred to herein as "1:1 Compound II citrate salt".

In another aspect, the present disclosure provides a pharmaceutical composition comprising 1:1 Compound I tris salt (or 1:1 Compound II tris salt or 1:1 Compound II citrate salt) and a pharmaceutically acceptable carrier.

The present disclosure provides a method of treating cardiometabolic and associated diseases, administering to a subject in need of such treatment a therapeutically effective amount of the salts of disclosed herein or the corresponding pharmaceutical compositions.

The present disclosure also provides a use of the salt of the disclosure or the pharmaceutical composition thereof comprising the same in any of the methods of the disclosure described above. In one embodiment, provided is the salt of the disclosure or a pharmaceutical composition thereof comprising the same for use in any of the method of the disclosure described herein. In another embodiment, provided is use of the salt of the disclosure or a pharmaceutical composition thereof comprising the same for the manufacture of a medicament for any of the method of the disclosure described. It should be understood that any embodiment of the present disclosure, including those described only in the Examples or claims, or only in one section of the specification, can be combined with one or more additional embodiments of the present disclosure, to the extent that such combinations are not expressly disclaimed or are improper.

DETAILED DESCRIPTION

The present disclosure is directed to a novel tris salt (i.e., 1:1 tris salt) of Compound I, a novel tris salt (i.e., 1:1 tris salt) of Compound II and a novel citrate salt (i.e., 1:1 citrate salt) of Compound II as well as polymorphic forms of each of the foregoing.

"Hydrated form" refers to a solid or a crystalline form of Compound I or Compound II in free base or a salt where water is combined with free base Compound (I) or the corresponding salt in a stoichiometric ratio (e.g., a molar ratio of Compound (I):water 1:1 or 1:2) as an integral part of the solid or a crystal. "Unhydrated form" refers to a form which has no stoichiometric ratio between water and the free base of Compound (I) or the corresponding salt of Compound (I), and water is not substantially (e.g., less that 10% by weight by Karl Fischer analysis) present in the solid form. The new solid forms disclosed in the present disclosure include hydrated forms and unhydrated forms.

As used herein, "crystalline" refers to a solid having a crystal structure wherein the individual molecules have a highly homogeneous regular three dimensional configuration.

The disclosed crystalline Compound I salts and/or Compound II salts can be crystals of a single crystal form or a mixture of crystals of different single crystalline forms. A single crystal form means the Compound I (or Compound II) is a single crystal or a plurality of crystals in which each crystal has the same crystal form.

For the crystalline forms of Compound I/Compound II salt disclosed herein, at least a particular percentage by weight of 1:1 Compound I/Compound II salt is in a single crystal form. Particular weight percentages include 85%, 86%, 87%, 88%, 89%, 90%, 91%, 92%, 93%, 94%, 95%, 96%, 97%, 98%, 99%, 99.5%, 99.9%, or a weight percentage of 70%-75%, 75%-80%, 80%-85%, 85%-90%, 90%-95%, 95%400%, 70-80%, 80-90%, 90-100% by weight of the Compound I/Compound II salt is in a single crystal form. It is to be understood that all values and ranges between these values and ranges are meant to be encompassed by the present disclosure.

When the crystalline Compound I/Compound II salt is defined as a specified percentage of one particular crystal form of the Compound I/Compound II salt, the remainder is made up of amorphous form and/or crystal forms other than the one or more particular forms that are specified. Examples of single crystal forms include 1:1 Compound I Tris salt (Form A), 1:1 Compound II Tris salt (Forms B and G) and 1:1 Compound II Citrate salt (Form A) characterized by one or more properties as discussed herein.

Both Compound I and Compound II have a chiral center. Compound I and Compound II in the salts and polymorphs disclosed herein are at least 80%, 90%, 99% or 99.9% by weight pure relative to the other stereoisomers, i.e., the ratio of the weight of the stereoisomer over the weight of all the stereoisomers.

Figure 1:
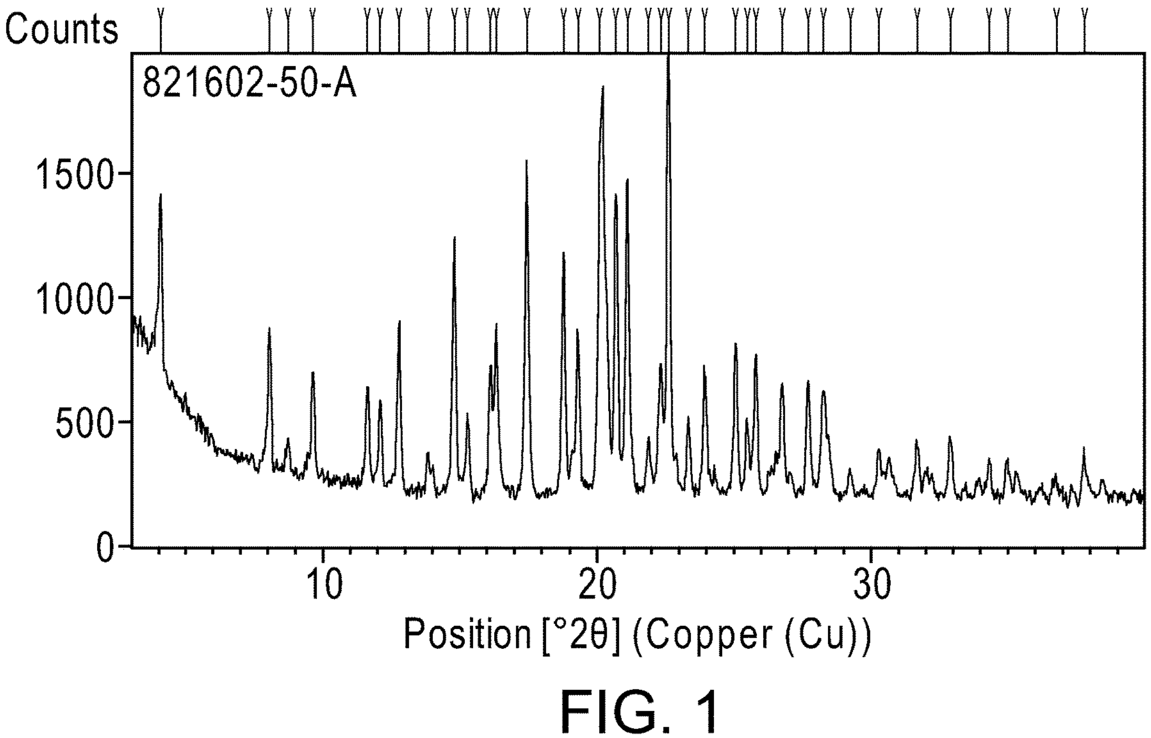
FIG. 1 shows the X-ray Powder Diffraction (XRPD) pattern of 1:1 Compound I Tris Salt (Form A).

The crystalline Compound I/Compound II salts disclosed herein exhibit strong, unique XRPD patterns with sharp peaks corresponding to angular peak positions in 20 and a flat baseline, indicative of a highly crystalline material (e.g., FIG. 1).

Characterization of 1:1 Compound I Tris Salt Crystalline Forms

In one embodiment, 1:1 Compound I Tris salt is a single crystalline form, Form A, characterized by an X-ray powder diffraction pattern which comprises peaks at 17.5°, 20.1°, 20.7°, 21.1°, and 22.6°±0.2 in 2θ. In another embodiment, Form A is characterized by an X-ray powder diffraction pattern which comprises at least three peaks (or four peaks) selected from 17.5°, 20.1°, 20.7°, 21.1°, and 22.6°±0.2 in 2θ. In yet another embodiment, Form A is characterized by an X-ray powder diffraction pattern which comprises peaks at 4.1°, 14.8°, 17.5°, 18.8°, 20.1°, 20.7°, 21.1°, and 22.6°±0.2 in 2θ. In yet another embodiment, Form A is characterized by an X-ray powder diffraction pattern which comprises peaks at 4.1°, 8.1°, 12.8°, 14.8°, 16.3°, 17.5°, 18.8°, 19.3°, 20.1°, 20.7°, 21.1°, 22.6°, 25.1°, and 25.8°±0.2 in 2θ. In yet another embodiment, Form A is characterized by an X-ray powder diffraction pattern substantially similar to FIG. 1.

It is well known in the crystallography art that, for any given crystal form, an angular peak position may vary slightly due to factors such as temperature variation, sample displacement, and the presence or absence of an internal standard. In the present disclosure, the variability of an angular peak position is ±0.2 in 2θ. In addition, the relative peak intensities for a given crystal form may vary due to differences in crystallite sizes and non-random crystallite orientations in sample preparation for XRPD analysis. It is well known in the art that this variability will account for the above factors without hindering the unequivocal identification of a crystal form.

In another embodiment, 1:1 Compound I Tris salt Form A is characterized by differential scanning calorimeter (DSC) peak phase transition temperatures of 173±3° C. (e.g., 174.3° C.).

Characterization of 1:1 Compound II Citrate Salt Crystalline Forms

In one embodiment, 1:1 Compound II citrate salt is a single crystalline form, Form A, characterized by an X-ray powder diffraction pattern which comprises peaks at 5.4°, 9.4°, 12.4°, 14.3°, and 17.8°±0.2 in 2θ. In another embodiment, Form A is characterized by an X-ray powder diffraction pattern which comprises at least three peaks (or four peaks) selected from 5.4°, 9.4°, 12.4°, 14.3°, and 17.8°±0.2 in 2θ. In yet another embodiment, Form A is characterized by an X-ray powder diffraction pattern which comprises peaks at 5.4°, 9.4°, 10.8°, 12.4°, 14.3°, 16.2°, 17.8°, 19.6°, and 24.9°±0.2 in 2θ. In yet another embodiment, Form A is characterized by an X-ray powder diffraction pattern which comprises peaks at 5.4°, 9.4°, 10.8°, 12.4°, 14.3°, 16.2°, 17.8°, 18.8°, 19.6°, 23.6°, and 24.9°±0.2 in 2θ. In yet another embodiment, Form A is characterized by an X-ray powder diffraction pattern substantially similar to FIG. 4.

In another embodiment, 1:1 Compound I Tris salt Form A is characterized by differential scanning calorimeter (DSC) peak phase transition temperatures of 170±3° C. (e.g., 169.9° C.).

Characterization of 1:1 Compound II Tris Salt Crystalline Forms

In one embodiment, 1:1 Compound II Tris salt is a single crystalline form, Form B, characterized by an X-ray powder diffraction pattern which comprises peaks at 4.1°, 14.7°, 18.8°, 20.1°, and 23.1°±0.2 in 2θ. In another embodiment, Form B is characterized by an X-ray powder diffraction pattern which comprises at least three peaks (or four peaks) selected from 4.1°, 14.7°, 18.8°, 20.1°, and 23.1°±0.2 in 2θ. In yet another embodiment, Form B is characterized by an X-ray powder diffraction pattern which comprises peaks at 4.1°, 8.2°, 14.7°, 16.4°, 18.8°, 20.1°, 20.7°, 21.3°, and 23.1°±0.2 in 2θ. In yet another embodiment, Form B is characterized by an X-ray powder diffraction pattern which comprises peaks at 4.1°, 8.2°, 14.7°, 16.4°, 18.8°, 19.1°, 20.1°, 20.7°, 21.3°, 23.1°, 24.1°, and 25.4°±0.2 in 2θ. In yet another embodiment, Form B is characterized by an X-ray powder diffraction pattern substantially similar to FIG. 6.

In another embodiment, 1:1 Compound II Tris salt Form B is characterized by differential scanning calorimeter (DSC) peak phase transition temperatures of 168±4° C. (e.g., 170.3° C.).

In one embodiment, 1:1 Compound II Tris salt is a single crystalline form, Form G, characterized by an X-ray powder diffraction pattern which comprises peaks at 6.2°, 7.6°, 13.1°, 13.4°, and 18.5°±0.2 in 2θ. In another embodiment, Form G is characterized by an X-ray powder diffraction pattern which comprises at least three peaks (or four peaks) selected from 6.2°, 7.6°, 13.1°, 13.4°, and 18.5°±0.2 in 2θ. In yet another embodiment, Form G is characterized by an X-ray powder diffraction pattern which comprises peaks at 6.2°, 7.6°, 13.1°, 13.4°, 18.5°, 21.5°, 23.7°, and 24.1°±0.2 in 2θ. In yet another embodiment, Form G is characterized by an X-ray powder diffraction pattern which comprises peaks at 6.2°, 7.6°, 13.1°, 13.4°, 18.0°, 18.5°, 20.8°, 21.5°, 23.7°, and 24.1°±0.2 in 2θ. In yet another embodiment, Form B is characterized by an X-ray powder diffraction pattern substantially similar to FIG. 8.

In another embodiment, 1:1 Compound II Tris salt Form G is characterized by differential scanning calorimeter (DSC) peak phase transition temperatures of 129.5±4° C.

Pharmaceutical Compositions

In another embodiment, disclosed herein are pharmaceutical compositions. Such pharmaceutical compositions comprise a salt of Compound I (or Compound II) described herein and a pharmaceutically acceptable carrier. Other pharmacologically active substances can also be present.

As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, sodium chloride, or polyalcohols such as mannitol, or sorbitol in the composition. Pharmaceutically acceptable substances such as wetting agents or minor amounts of auxiliary substances such as wetting or emulsifying agents, preservatives or buffers, which enhance the shelf life or effectiveness of the antibody or antibody portion.

The compositions of the present disclosure may be in a variety of forms. These include, for example, liquid, semi-solid and solid dosage forms, such as liquid solutions (e.g., injectable and infusible solutions), dispersions or suspensions, tablets, pills, powders, liposomes and suppositories. The form depends on the intended mode of administration and therapeutic application.

Typical compositions are in the form of injectable or infusible solutions, such as compositions similar to those used for passive immunization of humans with antibodies in general. One mode of administration is parenteral (e.g. intravenous, subcutaneous, intraperitoneal, intramuscular). In another embodiment, the antibody is administered by intravenous infusion or injection. In yet another embodiment, the antibody is administered by intramuscular or subcutaneous injection.

Oral administration of a solid dose form may be, for example, presented in discrete units, such as hard or soft capsules, pills, cachets, lozenges, or tablets, each containing a predetermined amount of at least one compound of the present disclosure. In another embodiment, the oral administration may be in a powder or granule form. In another embodiment, the oral dose form is sub-lingual, such as, for example, a lozenge. In such solid dosage forms, the compounds of any one of the formulae described above are ordinarily combined with one or more adjuvants. Such capsules or tablets may contain a controlled release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present disclosure comprises a parenteral dose form. "Parenteral administration" includes, for example, subcutaneous injections, intravenous injections, intraperitoneally, intramuscular injections, intrasternal injections, and infusion. Injectable preparations (i.e., sterile injectable aqueous or oleaginous suspensions) may be formulated according to the known art using suitable dispersing, wetting agents, and/or suspending agents.

In another embodiment, the present disclosure comprises a topical dose form.

"Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this present disclosure are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions.

Liposomes may also be used. Typical carriers include alcohol, water, mineral oil, liquid petrolatum, white petrolatum, glycerin, polyethylene glycol and propylene glycol. Penetration enhancers may be incorporated—see, for example, Finnin and Morgan, *J. Pharm. Sci.,* 88:955-958, 1999.

Formulations suitable for topical administration to the eye include, for example, eye drops wherein the compound of this present disclosure is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (i.e., absorbable gel sponges, collagen) and non-biodegradable (i.e., silicone) implants, wafers, lenses and particulate or vesicular systems, such as niosomes or liposomes. A polymer such as crossed linked polyacrylic acid, polyvinyl alcohol, hyaluronic acid, a cellulosic polymer, for example, hydroxypropylmethylcellulose, hydroxyethylcellulose, or methylcellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the compounds of the present disclosure are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present disclosure comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the present disclosure may be prepared by any of the well-known techniques of pharmacy, such as effective formulation and administration procedures.

The above considerations in regard to effective formulations and administration procedures are well known in the art and are described in standard textbooks. Formulation of drugs is discussed in, for example, Hoover, John E., *Remington's Pharmaceutical Sciences,* Mack Publishing Co., Easton, Pa., 1975; Liberman et al., Eds., *Pharmaceutical Dosage Forms,* Marcel Decker, New York, N.Y., 1980; and Kibbe et al., Eds., *Handbook of Pharmaceutical Excipients* ($3^{rd}$ Ed.), American Pharmaceutical Association, Washington, 1999.

Methods of Treatment

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

A "treatment" regime of a subject with an effective amount of the compound of the present disclosure may consist of a single administration, or alternatively comprise a series of applications. The length of the treatment period depends on a variety of factors, such as the severity of the disease, the age of the subject, the concentration and the activity of the compounds of the present disclosure, or a combination thereof. It will also be appreciated that the effective dosage of the compound used for the treatment or prophylaxis may increase or decrease over the course of a particular treatment or prophylaxis regime. Changes in dosage may result and become apparent by standard diagnostic assays known in the art. In some instances, chronic administration may be required.

In one aspect, the present disclosure provides a salt of Compound I (or Compound II), as described herein, for use in the prevention and/or treatment of cardiometabolic and associated diseases discussed herein, including T2DM, prediabetes, NASH, and cardiovascular disease.

In another aspect, the present disclosure provides a method of treating a disease for which an agonist of GLP-1R is indicated, in a subject in need of such prevention and/or treatment, comprising administering to the subject a therapeutically effective amount of a salt of Compound I (or Compound II), as described herein.

In another aspect, the present disclosure provides a use of a salt of Compound I (or Compound II), as described herein, for the manufacture of a medicament for treating a disease or condition for which an agonist of the GLP-1R is indicated.

In another aspect, the present disclosure provides a salt of Compound I (or Compound II), as described herein, for use in the treatment of a disease or condition for which an agonist of GLP-1R is indicated.

In another aspect, the present disclosure provides a pharmaceutical composition for the treatment of a disease or condition for which an agonist of the GLP-1R is indicated, comprising a salt of Compound I (or Compound II), as described herein.

The present disclosure also provides a pharmaceutical composition comprising a salt of Compound I (or Compound II), as described herein, for use in the treatment and/or prevention of cardiometabolic and associated diseases discussed herein, including T2DM, pre-diabetes, NASH, and cardiovascular disease.

In another aspect, the present disclosure provides a salt of Compound I (or Compound II), as described herein, for use in the treatment and/or treatment for cardiometabolic and associated diseases including diabetes (T1D and/or T2DM, including pre-diabetes), idiopathic T1D (Type lb), latent autoimmune diabetes in adults (LADA), early-onset T2DM (EOD), youth-onset atypical diabetes (YOAD), maturity onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, kidney disease (e.g., acute kidney disorder, tubular dysfunction, proinflammatory changes to the proximal tubules), diabetic retinopathy, adipocyte dysfunction, visceral adipose deposition, sleep apnea, obesity (including hypothalamic obesity and monogenic obesity) and related comorbidities (e.g., osteoarthritis and urine incontinence), eating disorders (including binge eating syndrome, bulimia nervosa, and syndromic obesity such as Prader-Willi and Bardet-Biedl syndromes), weight gain from use of other agents (e.g., from use of steroids and antipsychotics), excessive sugar craving, dyslipidemia (including hyperlipidemia, hypertriglyceridemia, increased total cholesterol, high LDL cholesterol, and low HDL cholesterol), hyperinsulinemia, NAFLD (including related diseases such as steatosis, NASH, fibrosis, cirrhosis, and hepatocellular carcinoma),cardiovascular disease, atherosclerosis (including coronary artery disease), peripheral vascular disease, hypertension, endothelial dysfunction, impaired vascular compliance, congestive heart failure, myocardial infarction (e.g. necrosis and apoptosis), stroke, hemorrhagic stroke, ischemic stroke, traumatic brain injury, pulmonary hypertension, restenosis after angioplasty, intermittent claudication, post-prandial lipemia, metabolic acidosis, ketosis, arthritis, osteoporosis, Parkinson's Disease, left ventricular hypertrophy, peripheral arterial disease, macular degeneration, cataract, glomerulosclerosis, chronic renal failure, metabolic syndrome, syndrome X, premenstrual syndrome, angina pectoris, thrombosis, atherosclerosis, transient ischemic attacks, vascular restenosis, impaired glucose metabolism, conditions of impaired fasting plasma glucose, hyperuricemia, gout, erectile dysfunction, skin and connective tissue disorders, psoriasis, foot ulcerations, ulcerative colitis, hyper apo B lipoproteinemia, Alzheimer's Disease, schizophrenia, impaired cognition, inflammatory bowel disease, short bowel syndrome, Crohn's disease, colitis, irritable bowel syndrome, prevention or treatment of Polycystic Ovary Syndrome and treatment of addiction (e.g., alcohol and/or drug abuse).

In certain embodiments, the disease or disorder is obesity, eating disorders, weight gain from use of other agents, excessive sugar craving, and dyslipidemia.

In certain embodiments, the disease or disorder is obesity.

In certain embodiments, the disease or disorder is prediabetes.

In certain embodiments, the disease or disorder is T2DM.

In certain embodiments, the disease or disorder is NASH.

In certain embodiments, the disease or disorder is NAFLD.

In certain embodiments, the disease or disorder is a cardiovescular disease, such as hypertension.

In another aspect, the present disclosure provides a method of enhancing or stimulating GLP-1R-mediated cAMP signaling with reduced β-arrestin/arrestin-2 recruitment, comprising administering a compound of any one of the formulae described above (e.g., Formulae I, II-A, III-A, and IV-A), or a pharmaceutically acceptable salt, stereoisomer, solvate, or hydrate thereof, as defined in any one of the embodiments described herein. This is partly based on the surprising finding that the compounds of the present disclosure, while being full agonists ofGLP-1R-mediated cAMP signaling, are partial agonists of β-arrestin recruitment to activated GLP-1R, compared to the natural GLP-1R ligand GLP-1, in that maximal β-arrestin recruitment to activated GLP-1R by the compounds of the present disclosure is lower than maximal β-arrestin recruitment by GLP-1. Such partial and/or biased agonists of GLP-1R for cAMP signaling may provide a more sustained cAMP signaling activity for better efficacy and lowered side effects.

Thus, the method of the present disclosure may be advantageously used for the treatment of any of the diseases or conditions described herein, such as type II diabetes (T2D) and related diseases.

In certain embodiments, the treatment elicits a glycemic benefit without concomitant increase, or at least reduced increase, in a GI side effect such as nausea, vomiting, or diarrhea. In certain embodiments, the treatment has greater tolerability compared to a control treatment that has normal or enhanced β-arrestin recruitment (such as β-arrestin recruitment by GLP-1).

Administration and Dosing

Typically, a compound of the present disclosure is administered in an amount effective to treat a condition as described herein. The compounds of the present disclosure can be administered as compound per se, or alternatively, as a pharmaceutically acceptable salt. For administration and dosing purposes, the compound per se or pharmaceutically acceptable salt thereof will simply be referred to as the compounds of the present disclosure.

The compounds of the present disclosure are administered by any suitable route in the form of a pharmaceutical composition adapted to such a route, and in a dose effective for the treatment intended. The compounds of the present disclosure may be administered orally, rectally, vaginally, parenterally, or topically.

The compounds of the present disclosure may be administered orally. Oral administration may involve swallowing, so that the compound enters the gastrointestinal tract, or buccal or sublingual administration may be employed by which the compound enters the bloodstream directly from the mouth.

In another embodiment, the compounds of the present disclosure may also be administered directly into the bloodstream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the present disclosure may also be administered topically to the skin or mucosa, that is, dermally or transdermally. In another embodiment, the compounds of the present disclosure can also be administered intranasally or by inhalation. In another embodiment, the compounds of the present disclosure may be administered rectally or vaginally. In another embodiment, the compounds of the present disclosure may also be administered directly to the eye or ear. The dosage regimen for the compounds of the present disclosure and/or compositions containing said compounds is based on a variety of factors, including the type, age, weight, sex and medical condition of the patient; the severity of the condition; the route of administration; and the activity of the particular compound employed. Thus the dosage regimen may vary widely. In one embodiment, the total daily dose of a compound of the present disclosure is typically from about 0.001 to about 100 mg/kg (i.e., mg compound of the present disclosure per kg body weight) for the treatment of the indicated conditions discussed herein. In another embodiment, total daily dose of the compound of the present disclosure is from about 0.01 to about 30 mg/kg, and in another embodiment, from about 0.03 to about 10 mg/kg, and in yet another embodiment, from about 0.1 to about 3 mg/kg. It is not uncommon that the administration of the compounds of the present disclosure will be repeated a plurality of times in a day (typically no greater than 4 times). Multiple doses per day typically may be used to increase the total daily dose, if desired. In certain embodiments, the patient is a human, such as a human with one of the treatable disease indications or disorders described elsewhere herein.

For oral administration, the compositions may be provided in the form of tablets containing 0.1, 0.5, 1.0, 2.5, 5.0, 10.0, 15.0, 25.0, 30.0 50.0, 75.0, 100, 125, 150, 175, 200, 250 and 500 milligrams of the active ingredient for the symptomatic adjustment of the dosage to the patient. A medicament typically contains from about 0.01 mg to about 500 mg of the active ingredient, or in another embodiment, from about 1 mg to about 100 mg of active ingredient. Intravenously, doses may range from about 0.01 to about 10 mg/kg/minute during a constant rate infusion.

Suitable subjects or patients according to the present disclosure include mammalian subjects, including human, or non-human mammals such as primates, rodents (mice, rats, hamsters, rabbits etc). In one embodiment, humans are suitable subjects. Human subjects may be of either gender and at any stage of development. In certain embodiments, the human is a child less than 18 years old, 15 years old or around 14 years old, 12 years old, 10 years old, or less than 5 years old.

Co-Administration

The compounds of the present disclosure can be used alone, or in combination with other therapeutic agents. The present disclosure provides any of the uses, methods or compositions as defined herein wherein the compound of any embodiment of any one of the formulae described above herein, or pharmaceutically acceptable salt thereof, or pharmaceutically acceptable solvate of said compound or salt, is used in combination with one or more other therapeutic agent discussed herein.

The administration of two or more compounds "in combination" means that all of the compounds are administered closely enough in time that each may generate a biological effect in the same time frame. The presence of one agent may alter the biological effects of the other compound(s). The two or more compounds may be administered simultaneously, concurrently or sequentially. Additionally, simultaneous administration may be carried out by mixing the compounds prior to administration or by administering the compounds at the same point in time but as separate dosage forms at the same or different site of administration.

The phrases "concurrent administration," "co-administration," "simultaneous administration," and "administered simultaneously" mean that the compounds are administered in combination.

In another embodiment, the present disclosure provides methods of treatment that include administering compounds of the present present disclosure in combination with one or more other pharmaceutical agents, wherein the one or more other pharmaceutical agents may be selected from the agents discussed herein.

In one embodiment, the compounds of this present disclosure are administered with an anti-diabetic agent including but not limited to a biguanide (e.g., metformin), a sulfonylurea (e.g., tolbutamide, glibenclamide, gliclazide, chlorpropamide, tolazamide, acetohexamide, glyclopyramide, glimepiride, or glipizide), a thiazolidinedione (e.g., pioglitazone, rosiglitazone, or lobeglitazone), a glitazar (e.g., saroglitazar, aleglitazar, muraglitazar or tesaglitazar), a meglitinide (e.g., nateglinide, repaglinide), a dipeptidyl peptidase 4 (DPP-4) inhibitor (e.g., sitagliptin, vildagliptin, saxagliptin, linagliptin, gemigliptin, anagliptin, teneligliptin, alogliptin, trelagliptin, dutogliptin, or omarigliptin), a glitazone (e.g., pioglitazone, rosiglitazone, balaglitazone, rivoglitazone, or lobeglitazone), a sodium-glucose linked transporter 2 (SGLT2) inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a GPR40 agonist (FFAR1/FFA1 agonist, e.g. fasiglifam), glucose-dependent insulinotropic peptide (GIP) and analogues thereof, an alpha glucosidase inhibitor (e.g. voglibose, acarbose, or miglitol), or an insulin or an insulin analogue, including the pharmaceutically acceptable salts of the specifically named agents and the pharmaceutically acceptable solvates of said agents and salts.

In another embodiment, the compounds of this present disclosure are administered with an anti-obesity agent including but not limited to peptide YY or an analogue thereof, a neuropeptide Y receptor type 2 (NPYR2) agonist, a NPYR1 or NPYRS antagonist, a cannabinoid receptor type 1 (CB1R) antagonist, a lipase inhibitor (e.g., orlistat), a human proislet peptide (HIP), a melanocortin receptor 4 agonist (e.g., setmelanotide), a melanin concentrating hormone receptor 1 antagonist, a farnesoid X receptor (FXR) agonist (e.g. obeticholic acid), zonisamide, phentermine (alone or in combination with topiramate), a norepinephrine/dopamine reuptake inhibitor (e.g., buproprion), an opioid receptor antagonist (e.g., naltrexone), a combination of norepinephrine/dopamine reuptake inhibitor and opioid receptor antagonist (e.g., a combination of bupropion and naltrexone), a GDF-15 analog, sibutramine, a cholecystokinin agonist, amylin and analogues therof (e.g., pramlintide), leptin and analogues thereof (e.g., metroleptin), a serotonergic agent (e.g., lorcaserin), a methionine aminopeptidase 2 (MetAP2) inhibitor (e.g., beloranib or ZGN-1061), phendimetrazine, diethylpropion, benzphetamine, an SGLT2 inhibitor (e.g., empagliflozin, canagliflozin, dapagliflozin, ipragliflozin, Ipragliflozin, tofogliflozin, sergliflozin etabonate, remogliflozin etabonate, or ertugliflozin), an SGLTL1 inhibitor, a dual SGLT2/SGLT1 inhibitor, a fibroblast growth factor receptor (FGFR) modulator, an AMP-activated protein kinase (AMPK) activator, biotin, a MAS receptor modulator, or a glucagon receptor agonist (alone or in combination with another GLP-1R agonist, e.g., liraglutide, exenatide, dulaglutide, albiglutide, lixisenatide, or semaglutide), including the pharmaceutically acceptable salts of the specifically named agents and the pharmaceutically acceptable solvates of said agents and salts.

In another embodiment, the compounds of this present disclosure are administered with an agent to treat NASH including but not limited to PF-05221304, an FXR agonist (e.g., obeticholic acid), a PPAR a/6 agonist (e.g., elafibranor), a synthetic fatty acid-bile acid conjugate (e.g., aramchol), a caspase inhibitor (e.g., emricasan), an anti-lysyl oxidase homologue 2 (LOXL2) monoclonal antibody (e.g., simtuzumab), a galectin 3 inhibitor (e.g., GR-MD-02), a MAPK5 inhibitor (e.g., GS-4997), a dual antagonist of chemokine receptor 2 (CCR2) and CCR5 (e.g., cenicriviroc), a fibroblast growth factor 21 (FGF21) agonist (e.g., BMS-986036), a leukotriene D4 (LTD4) receptor antagonist (e.g., tipelukast), a niacin analogue (e.g., ARI 3037M0), an ASBT inhibitor (e.g., volixibat), an acetyl-CoA carboxylase (ACC) inhibitor (e.g., NDI 010976), a ketohexokinase (KHK) inhibitor, a diacylglyceryl acyltransferase 2 (DGAT2) inhibitor, a CB1 receptor antagonist, an anti-CB1R antibody, or an apoptosis signal-regulating kinase 1 (ASK1) inhibitor, including the pharmaceutically acceptable salts of the specifically named agents and the pharmaceutically acceptable solvates of said agents and salts.

These agents and compounds of the present disclosure can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride;

hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or Igs; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Liposomes containing these agents and/or compounds of the present disclosure are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

These agents and/or the compounds of the present disclosure may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy,* $20^{th}$ Ed., Mack Publishing (2000).

Sustained-release preparations may be used. Suitable examples of sustained-release preparations include semipermeable matrices of solid hydrophobic polymers containing the compound of any one of the formulae described above, which matrices are in the form of shaped articles, e.g., films, or microcapsules. Examples of sustained-release matrices include polyesters, hydrogels (for example, poly (2-hydroxyethyl-methacrylate), or 'poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as those used in LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for intravenous administration must be sterile. This is readily accomplished by, for example, filtration through sterile filtration membranes. Compounds of the present disclosure are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the present disclosure with IntralipidTM or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits

Another aspect of the present disclosure provides kits comprising the compound of any one of the formulae described above or pharmaceutical compositions comprising the compound of any one of the formulae described above of the present disclosure. A kit may include, in addition to the compound of any one of the formulae described above, of the present disclosure or pharmaceutical composition thereof, diagnostic or therapeutic agents. A kit may also include instructions for use in a diagnostic or therapeutic method. In some embodiments, the kit includes the compound of any one of the formulae described above, or a pharmaceutical composition thereof and a diagnostic agent. In other embodiments, the kit includes the compound of any one of the formulae described above, or a pharmaceutical composition thereof.

In yet another embodiment, the present disclosure comprises kits that are suitable for use in performing the methods of treatment described herein. In one embodiment, the kit contains a first dosage form comprising one or more of the compounds of the present disclosure in quantities sufficient to carry out the methods of the present disclosure. In another embodiment, the kit comprises one or more compounds of the present disclosure in quantities sufficient to carry out the methods of the present disclosure and a container for the dosage and a container for the dosage.

Preparation

The compounds of any one of the formulae described above, may be prepared by the general and specific methods described below, using the common general knowledge of one skilled in the art of synthetic organic chemistry. Such common general knowledge can be found in standard reference books such as *Comprehensive Organic Chemistry,* Ed. Barton and Ollis, Elsevier; *Comprehensive Organic Transformations: A Guide to Functional Group Preparations,* Larock, John Wiley and Sons; and *Compendium of Organic Synthetic Methods,* Vol. I-XII (published by Wiley-Interscience). The starting materials used herein are commercially available or may be prepared by routine methods known in the art.

In the preparation of the compounds of any one of the formulae described above, it is noted that some of the preparation methods described herein may require protection of remote functionality (e.g., primary amine, secondary amine, carboxyl in any one of the formulae described above precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see Greene, *Protective Groups in Organic Synthesis,* John Wiley & Sons, New York, 1991.

For example, certain compounds contain primary amines or carboxylic acid functionalities which may interfere with reactions at other sites of the molecule if left unprotected.

Accordingly, such functionalities may be protected by an appropriate protecting group which may be removed in a subsequent step. Suitable protecting groups for amine and carboxylic acid protection include those protecting groups commonly used in peptide synthesis (such as N-t-butoxycarbonyl (Boc), benzyloxycarbonyl (Cbz), and 9-fluorenylmethylenoxycarbonyl (Fmoc) for amines, and lower alkyl or benzyl esters for carboxylic acids) which are generally not chemically reactive under the reaction conditions described and can typically be removed without chemically altering other functionality in the any one of the formulae described above compounds.

The Schemes described below are intended to provide a general description of the methodology employed in the preparation of the compounds of the present present disclosure. Some of the compounds of the present present disclosure may contain single or multiple chiral centers with the stereochemical designation (R) or (S). It will be apparent to one skilled in the art that all of the synthetic transformations can be conducted in a similar manner whether the materials are enantioenriched or racemic. Moreover, the resolution to the desired optically active material may take place at any desired point in the sequence using well known methods such as described herein and in the chemistry literature.

Amine compounds prepared via methods described herein can be alkylated with a protected 2-bromoacetate in the presence of a suitable base such as $K_2CO_3$, $Et_3N$, NaH or LiHMDS in a polar aprotic solvent such as but not limited to DMF, DMAc, DMSO or NMP to deliver compounds. Standard ester hydrolysis can be performed to provide acids. If $Pg^2$ is t-butyl, standard acidic deprotection methods such as TFA/DCM, HCl/1,4-dioxane, HCl/EtOAc or other suitable conditions may be used to deliver acids.

Experimental

The solvent abbreviations are listed in the table below.

| Abbreviation | Solvent |
|---|---|
| MeOH | Methanol |
| EtOH | Ethanol |
| IPA | Isopropyl alcohol |
| MIBK | Methyl isobutyl ketone |
| EtOAc | Ethyl acetate |
| IPAc | Isopropyl acetate |
| MTBE | Methyl tert-butyl ether |
| THF | Tetrahydrofuran |
| ACN | Acetonitrile |
| DCM | Dichloromethane |
| DMSO | Dimethylsulfoxide |
| DMAc | Dimethylacetamide |
| NMP | Methyl-2-pyrrolidinone |
| 2-MeTHF | 2-Methyltetrahydrofuran |

Analysis Conditions

X-Ray Powder Diffraction (XRPD)

For XRPD analysis, PANalytical Empyrean/X' Pert3 X-ray powder diffractometers were used. The XRPD parameters used are listed in the table below.

XRPD parameters

| Parameters | Empyrean | X' Pert3 | X' Pert3 |
|---|---|---|---|
| X-Ray wavelength | Cu, Kα, Kα1 (Å): 1.540598, Kα2 (Å): 1.544426 Kα2/Kα1 intensity ratio: 0.50 | Cu, Kα, Kα1 (Å): 1.540598, Kα2 (Å): 1.544426 Kα2/Kα1 intensity ratio: 0.50 | Cu, Kα, Kα1 (Å): 1.540598, Kα2 (Å): 1.544426 Kα2/Kα1 intensity ratio: 0.50 |
| X-Ray tube setting | 45 kV, 40 mA | 45 kV, 40 mA | 45 kV, 40 mA |
| Divergence slit | Automatic | 1/8° | 1/8° |
| Scan mode | Continuous | Continuous | Continuous |
| Scan range (2θ/°) | 3-40 | 3-40 | 3-40 |
| Step size (2θ/°) | 17.780 | 46.665 | 39.525 |
| Scan step time (s) | 0.0167 | 0.0263 | 0.0263 |
| Test time (s) | 5 min 30 s | 5 min 04 s | 4 min 27 s |

Single Crystal X-Ray Diffraction (SCXRD)

SCXRD Instrument Parameters

| Instrument | Rigaku XtaLAB Synergy R |
|---|---|
| X-Ray sources generator | MicroMax-007HF X-ray source (Cu/kα: 1.54184 Å) |
| Detector | HyPix 6000HE detector |
| Goniometer | Four-circle Kappa Goniometer |
| Low Temperature Devices | Cryostream-700 (Oxford Cryosystems) |
| Software package | CrysAlisPro (V1.171.40.14e) |

Thermogravimetric Analysis and Differential Scanning calorimetry (TGA & DSC)

TGA data were collected using a TA Q5000/Discovery 5500 TGA from TA Instruments. DSC was performed using a TA Q2000/Discovery 2500 DSC from TA Instruments. Detailed parameters used are listed in the table below.

Parameters for TGA and DSC Test

| Parameters | TGA | DSC |
|---|---|---|
| Method | Ramp | Ramp/Custom |
| Sample pan | Aluminum, open | Aluminum, crimped/open |
| Temperature | RT-Target temperature | 25° C.-Target temperature |
| Heating rate | 10° C./min | 10° C./min |
| Purge gas | $N_2$ | $N_2$ |

$^1$H-Nuclear Magnetic Resonance Spectroscopy ($^1$H-NMR)

$^1$H solution NMR was collected on Bruker 400M NMR Spectrometer using DMSO-$_{d6}$.

Dynamic Vapor Sorption (DVS)

DVS was measured via a SMS (Surface Measurement Systems) DVS Intrinsic. The relative humidity at 25° C. were calibrated against deliquescence point of LiCl, $Mg(NO_3)_2$ and KCl. Parameters for DVS test are listed in the table below.

Parameters for DVS Test

| Parameters | DVS |
|---|---|
| Temperature | 20, 25, 30° C. |
| Sample size | 10-20 mg |
| Gas and flow rate | $N_2$, 200 mL/min |
| dm/dt | 0.002%/min |
| Min. Dm/dtstabilityduration | 10 min |
| Max. equilibrium time | 180 min |
| RH range | 0% RH-95% RH |
| RH step size | 10% (0% RH-90% RH, 90% RH-0% RH) 5% (90% RH-95% RH, 95% RH-90% RH) |

High Performance Liquid Chromatography (HPLC)

Agilent 1260 HPLC was used and detailed chromatographic conditions are listed in the table below.

Chromatographic Conditions and Parameters

| Parameters | Agilent 1260 Detector | |
|---|---|---|
| Column | ZORBAX SB-CN, 150 × 4.6 mm, 3.5 μm | |
| Mobile phase | A: 0.02M phosphate solution (pH 1.8) B: ACN | |
| | Time (min) | % B |
| Gradient table | 0.0 | 20 |
| | 5.0 | 40 |
| | 20.0 | 80 |
| | 20.1 | 20 |
| | 25.0 | 20 |
| Run time | 25.0 min | |
| Post time | 0.0 min | |
| Flow rate | 1.0 mL/min | |
| Injection volume | 10 μL | |
| Detector wavelength | UV at 220 nm | |
| Column temperature | 35° C. | |
| Sampler temperature | RT | |
| Diluent | $ACN/H_2O$ = 1:1 (v:v) | |

EXAMPLE 1
Synthesis of (S)-2-((4-(3-((4-chloro-2-fluorobenzyl)oxy)phenyl)-3,6-dihydropyridin-1(2H)-yl)methyl)-1-(oxetan-2-ylmethyl)-1H-benzo[d]imidazole-6-carboxylic acid (Compound I)
Compound I
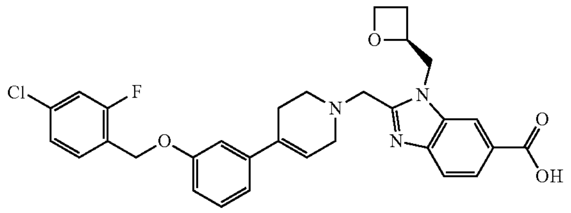
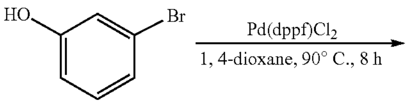
1
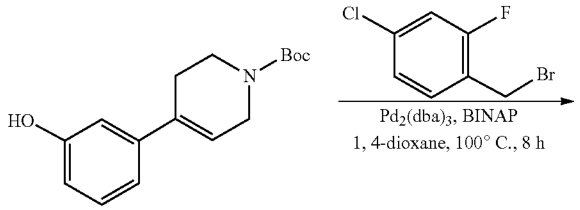
2
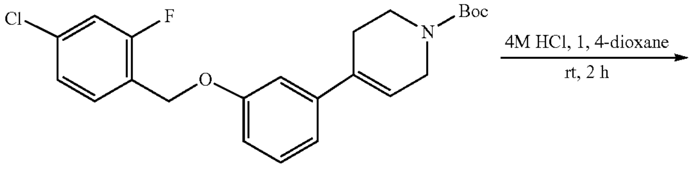
3
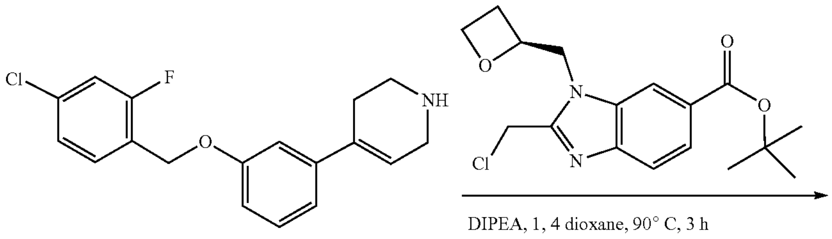
4
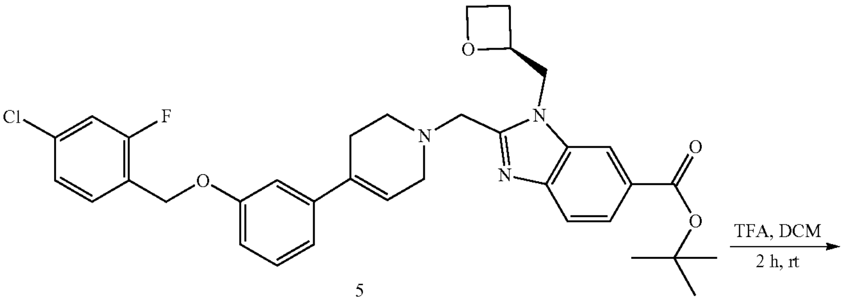
5

-continued

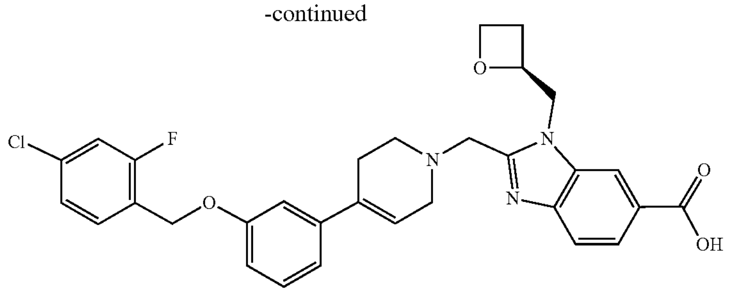

Compound I

Step 1

To a solution of 3-bromophenol (1.0 g, 5.8 mmol) in 1,4-dioxane (50 mL) was added tert-butyl 4-(4,4,5,5-tetramethyl-1,3,2-dioxaborolan-2-yl)-3,6-dihydropyridine-1(2H)-carboxylate (1.9 g, 6.4 mmol), and $Cs_2CO_3$(3.8 g,11.6 mmol) and Pd(dppf)$Cl_2$ (416 mg, 0.58 mmol). The mixture was stirred under nitrogen at 90° C. for 8 h. The mixture was filtered though Celite to give a solution, diluted with water (150 mL) and extracted with ethyl acetate (150 mL×3), the combine organic was washed with brine (150 mL×3), dried and concentrated in vacuo to give crude product. The crude product was purified by Pre-TLC (PE:EA=2:1) to give tert-butyl 4-(3-hydroxyphenyl)-3,6-dihydropyridine-1(2H)-carboxylate (1.51 g, 94% yield) as a white solid. LCMS: $[M+H]^+$=221, Retention time (10 mM $NH_4HCO_3$)=1.81 min.

Step 2

To a solution of tert-butyl 4-(3-hydroxyphenyl)-3,6-dihydropyridine-1(2H)-carboxylate (275 mg, 1.0 mmol) in 1,4-dioxane (10mL) was added 1-(bromomethyl)-4-chloro-2-fluorobenzene (223 mg, 1.0 mmol) and Pd2(dba)3 (91.5 mg, 0.1 mmol) and BINAP(62.2 mg,0.1 mmol). The mixture was stirred under nitrogen at 100° C. for 8 h. The reaction was cooled to rt and the reaction was diluted with water (150 mL), extracted with ethyl acetate (150 mL×3), The combine organic was washed with brine (150 mL×3), dried and concentrated in vacuo to give crude product. Then the crude product was purified by Pre-TLC (PE:EA=3:1) to give tert-butyl 4-(3-((4-chloro-2-fluorobenzyl)oxy)phenyl)-3,6-dihydropyridine-1(2H)-carboxylate (241 mg, 57.8% yield) as a yellow oil. LCMS: $[M+H]^+$=363, Retention time (10 mM $NH_4HCO_3$)=2.04 min.

Step 3

To a solution of tert-butyl 4-(3-((4-chloro-2-fluorobenzyl)oxy)phenyl)-3,6-dihydropyridine-1(2H)-carboxylate (322 mg, 0.77 mmol) in DCM (10 mL) was added HCl/1, 4dioxane(1.2 mL). The mixture was stirred at rt for 2 h. The reaction was diluted with water (50 mL) and extracted with ethyl acetate (50 mL×3), The combine organic was washed with brine (50 mL×3), dried and concentrated in vacuo to give crude product, which was purified by Pre-TLC (PE:EA=5:1) to give 4-(3-((4-chloro-2-fluorobenzyl)oxy)phenyl)-1,2,3,6-tetrahydropyridine (198 mg) as a yellow oil. LCMS: $[M+H]^+$=318, Retention time (10 mM $NH_4HCO_3$)=1.61 min.

Step 4

To a solution of 4-(3-((4-chloro-2-fluorobenzyl)oxy)phenyl)-1,2,3,6-tetrahydropyridine (90 mg, 0.28 mmol) in 1,4-dioxane(10 mL) was added tert-butyl (S)-2-(chloromethyl)-1-(oxetan-2-ylmethyl)-1H-benzo[d]imidazole-6-carboxylate (85 mg, 0.28 mmol) and added DIPEA (0.3 mL,1.4 mol). The mixture was stirred at 90° C. for 3 h. The reaction was diluted with water (100 mL) and extracted with ethyl acetate (100 mL×3), the combined organic layers were washed with brine (100 mL×3), dried and concentrated in vacuo to give crude product, which was purified by pre-TLC to give tert-butyl (S)-2-((4-(3-((4-chloro-2-fluorobenzyl)oxy)phenyl)-3,6-dihydropyridin-1(2H)-yemethyl)-1-(oxetan-2-ylmethyl)-1H-benzo[d]imidazole-6-carboxylate (80 mg, 46% yield) as a yellow solid. LCMS: $[M+H]^+$=618, Retention time (10mM $NH_4HCO_3$)=2.36 min.

Step 5

To a solution of tert-butyl (S)-2-((4-(3-((4-chloro-2-fluorobenzyl)oxy)phenyl)-3,6-dihydropyridin-1(2H)-yl)methyl)-1-(oxetan-2-ylmethyl)-1H-benzo[d]imidazole-6-carboxylate (80 mg, 0.13 mmol) in DCM (12 mL) was added TFA (2 mL, 26.93 mmol). The mixture was stirred at rt for 3 h. The reaction was concentrated in vacuo to give crude product, which was purified by Pre-HPLC ($NH_4HCO_3$) to give (S)-2-((4-(3-((4-chloro-2-fluorobenzyl)oxy)phenyl)-3,6-dihydropyridin-1(2H)-ypmethyl)-1-(oxetan-2-ylmethyl)-1H-benzo[d]imidazole-6-carboxylic acid (18.5 mg, 25% yield) as white solid. LCMS: $[M+H]^+$=562.0, Retention time (10 mM $NH_4HCO_3$)=1.40 min.

$^1H$ NMR (400 MHz, MeOD) δ 8.21-8.20 (brs, 1H), 7.97 (dd, J=8.5, 1.4 Hz, 1H), 7.62 (d, J=8.5 Hz, 1H), 7.54 (t, J=8.2 Hz, 1H), 7.25 (ddd, J=6.3, 5.6, 2.0 Hz, 3H), 7.11-7.02 (m, 2H), 6.89 (dd, J=7.3, 1.9 Hz, 1H), 6.13-6.12 (brs, 1H), 5.28 (dd, J=9.4, 5.0 Hz, 1H), 5.13 (s, 2H), 4.92 (d, J=7.1 Hz, 1H), 4.77-4.71 (m, 1H), 4.63 (dd, J=13.4, 8.2 Hz, 1H), 4.53-4.46 (m, 1H), 4.14 (d, J=13.6 Hz, 1H), 4.03 (d, J=13.6 Hz, 1H), 3.25 (d, J=2.4 Hz, 2H), 2.80 (ddd, J=22.5, 12.9, 7.2 Hz, 3H), 2.62-2.48 (m, 3H).

EXAMPLE 2
Synthesis of (S)-2-((6-((4-cyano-2-fluorobenzyl)oxy)-3',6'-dihydro-[2,4'-bipyridin]-1'(2'H)-yl)methyl)-1-(oxetan-2-ylmethyl)-1H-benzo[d]imidazole-6-carboxylic acid (Compound II)
Compound II
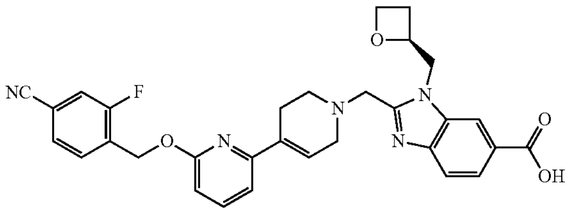
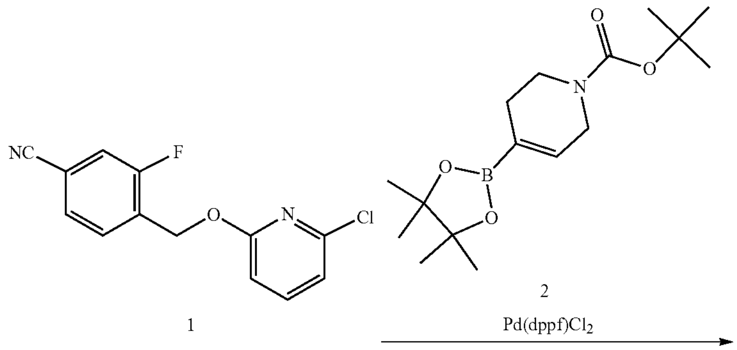
1
2
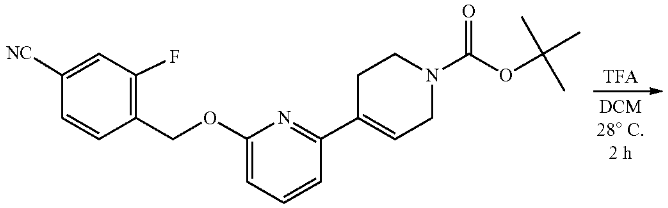
3
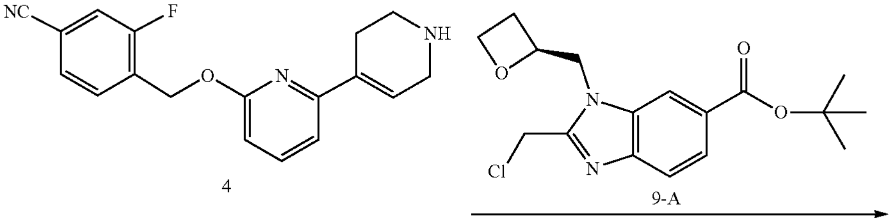
4
9-A -continued

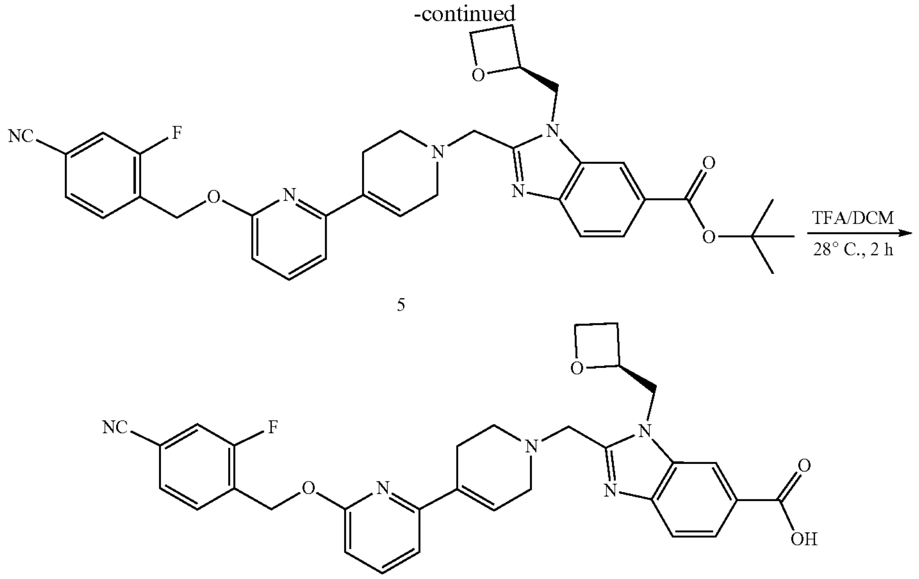

5

Compound II

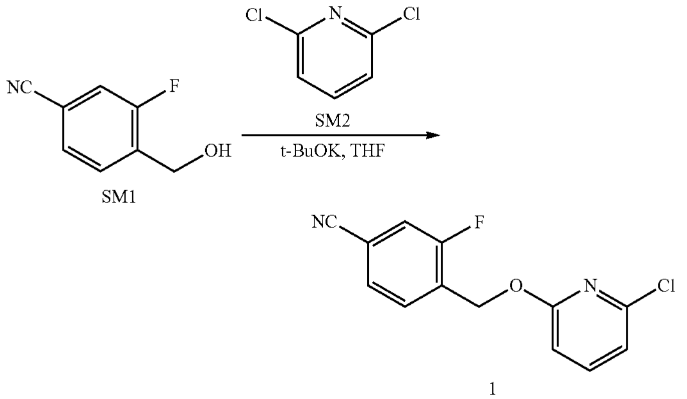

SM1

1

Step 1

To a stirred suspension of t-BuOK (31.3 g, 279.7 mmol) in THF (500 mL) was added 3-fluoro-4-(hydroxymethyl) benzonitrile (28.1 g, 186.5 mmol) portion wise between 10-15° C. The mixture was stirred at 15° C. for 45 min and 2,6-dichloropyridine (23.0 g, 155.4 mmol) was added in several portions to the reaction mixture at 15° C. and the mixture was stirred at 15° C. for 18 h.The mixture was poured into aq. $NH_4Cl$ (1000 mL). EtOAc (1000 mL) was added and the mixture was stirred for 15 min. The mixture was filtered through a pad of Celite. The organic layer was separated and the aq. layer extracted with EtOAc (2×600 mL). The combined organic layers were washed with brine (500 mL). dried over $Na_2SO_4$, filtered and concentrated under reduced pressure. The crude product was purified by column chromatography on silica gel (PE/EtOAc=10/1) to obtain 4-((6-chloropyridin-2-yloxy)methyl)-3-fluorobenzonitrile (26.0 g, 64% yield) as light yellow solid.

$^1$H NMR (400 MHz, CDCl3) δ 7.67-7.63 (t, J=7.6 Hz, 1H), 7.59-7.55 (t, J=7.6 Hz, 1H), 7.49-7.46 (dd, J1=8.0 Hz, J2=1.2 Hz, 1H), 7.40-7.37 (dd, J1=9.2 Hz, J2=1.2 Hz,1H), 6.97-6.95 (d, J=7.6 Hz, 1H), 6.75-6.73 (d, J=8.4 Hz, 1H), 5.48 (s, 2H).

Step 1a

A mixture of 4-[(6-chloro-2-pyridyl)oxymethyl]-3-fluoro-benzonitrile (1 g, 3.81 mmol), tert-butyl 4-(4,4,5,5-tetramethyl-1,3,2-dioxaborolan-2-yl)-3,6-dihydro-2H-pyridine-1-carboxylate (1.29 g, 4.19 mmol), Pd(dppf)$Cl_2$ (278.3 mg, 0.38 mmol) and $NaHCO_3$ (479.69 mg, 5.71 mmol) in dioxane (20 mL) and $H_2O$ (4 g, 222.22 mmol) was stirred for 2 h at 90° C. under $N_2$, until the reaction was complete as indicated by LCMS. The reaction mixture was filtered through a pad of Celite with EtOAc, and the combined organics were concentrated in vacuo, purified by silica gel chromatography (Hexanes/EtOAc=0-11%) to give the desired product tert-butyl 4-[6-[(4-cyano-2-fluoro-phenyl) methoxy]-2-pyridyl]-3,6-dihydro-2H-pyridine-1-carboxylate (1.5 g, 3.63 mmol, 95.4% yield) as pale yellow liquid. LCMS: $[M+H]^+$=410.1; Retention time (10 mM $NH_4HCO_3$) =2.22 min.

Step 2

To a solution of tert-butyl 4-[6-[(4-cyano-2-fluoro-phenyl)methoxy]-2-pyridyl]-3,6-dihydro-2H-pyridine-1-carboxylate (1.5 g, 3.66 mmol) in DCM (20 mL) was added slowly TFA (7.40 g, 64.90 mmol, 5 mL). The reaction was stirred at 28° C. for 2 h. After completion of the reaction as determined by LCMS, reaction mixture was concentrated in vacuo to afford 3-fluoro-4-[[6-(1,2,3,6-tetrahydropyridin-4-yl)-2-pyridyl]oxymethyl]benzonitrile (1.8 g, 3.94 mmol) TFA salt as a pale yellowish liquid. The crude product was used directly next step without further purification. LCMS: $[M+H]^+$=310.1; Retention time (0.01% TFA)=1.42 min.

Step 3

A mixture of 3-fluoro-4-[[6-(1,2,3,6-tetrahydropyridin-4-yl)-2-pyridyl]oxymethyl]-benzonitrile (340 mg, 0.80 mmol), tert-butyl 2-(chloromethyl)-3-[[(2S)-oxetan-2-yl]methyl]benzimidazole-5-carboxylate (225 mg, 670 mmol, the synthesis is disclosed in international application WO2018/109607, which is incorporated herein by reference) and DIPEA (216.42 mg, 1.67 mmol) in Dioxane (10 mL) was stirred for 1 h at 90° C., until the reaction was complete as indicated by LCMS, the reaction mixture was concentrated in vacuo, purified by silica gel chromatography (Hexanes/EtOAc=20:1) to give the desired product tert-butyl 2-[[4-[6-[(4-cyano-2-fluoro-phenyl)methoxy]-2-pyridyl]-3,6-dihydro-2H-pyridin-1-yl]methyl]-3-[[(2S)-oxetan-2-yl]methyl]benzimidazole-5-carboxylate (366 mg, 0.31 mmol) as pale brown solid. LCMS: $[M+H]^+$=610.0; Retention time (10 mM $NH_4H\ CO_3$)=1.87 min.

Step 4

To a solution of tert-butyl 2-[[4-[6-[(4-cyano-2-fluoro-phenyl)methoxy]-2-pyridyl]-3,6-dihydro-2H-pyridin-1-yl]methyl]-3-[[(2S)-oxetan-2-yl]methyl]benzimidazole carboxylate (180 mg, 0.30 mmol) in DCM (6 mL) was added slowly TFA (2.96 g, 25.96 mmol, 2 mL) in DCM (2 mL) at 28° C. and stirred for 1 h. After completion of the reaction as judged by LCMS, reaction mixture was concentrated in vacuo, the crude product was purified by Prep-HPLC (10 mM $NH_4HCO_3$) to afford (S)-2-((6-((4-cyano-2-fluorobenzyl)oxy)-3', 6'-dihydro-[2,4'-bipyridin]-1'(2'H)-yl)methyl)-1-(oxetan-2-ylmethyl)-1H-benzo[d]imidazole-6-carboxylic acid (54 mg, 33% yield) as a white solid. LCMS: $[M+H]^+$=554.2; Retention time (10 mM $NH_4HCO_3$)=1.42 min.

$^1$H NMR (400 MHz, DMSO-d6) δ 12.73-12.72 (brs, 1H), 8.27-8.26 (brs, 1H), 7.90 (d, J=10.3 Hz, 1H), 7.81 (dd, J=8.5, 1.5 Hz, 1H), 7.69 (dt, J=13.2, 8.0 Hz, 4H), 7.10 (d, J=7.5 Hz, 1H), 6.85-6.61 (m, 2H), 5.49 (s, 2H), 5.15-5.02 (m, 1H), 4.80 (dd, J=15.2, 7.3 Hz, 1H), 4.71-4.60 (m, 1H), 4.40 (ddt, J=11.9, 8.9, 6.0 Hz, 2H), 4.07 (d, J=13.5 Hz, 1H), 3.91 (d, J=13.5 Hz, 1H), 3.28-3.17 (m, 2H), 2.73 (d, J=2.5 Hz, 2H), 2.70-2.60 (m, 1H), 2.43-2.42 (m, 2H), 2.44-2.34 (m, 1H).

EXAMPLE 3

Preparations and Characterization of Crystalline Form of 1:1 Compound I Tris Salt (Form A)

3.1.1 Preparation Method

A solution of 500.9 mg of free form of Compound I was dissolved in 20 mL Acetone/$H_2O$ (9:1, v:v). In the meatime, an equimolar Tris (107.9 mg) was dissolved in 2.5 mL $H_2O$. The obtained Tris solution was added to the free form of Compound I solution dropwise and stirred at room temperature (RT, ~1000 rpm). The obtained slurry was stirred continuously for 17 hours at RT, then it was cooled down to 5° C. and stirred for another 4 hours. The solid in the mixture was isolated by centrifugation and vacuum dried at RT for 20 hours to obtain 445.9 mg of the desired product (yield ~73.2%).

The solid obtained was further characterized by XRPD (FIG. 1 and Table 1).

Figure 2A:
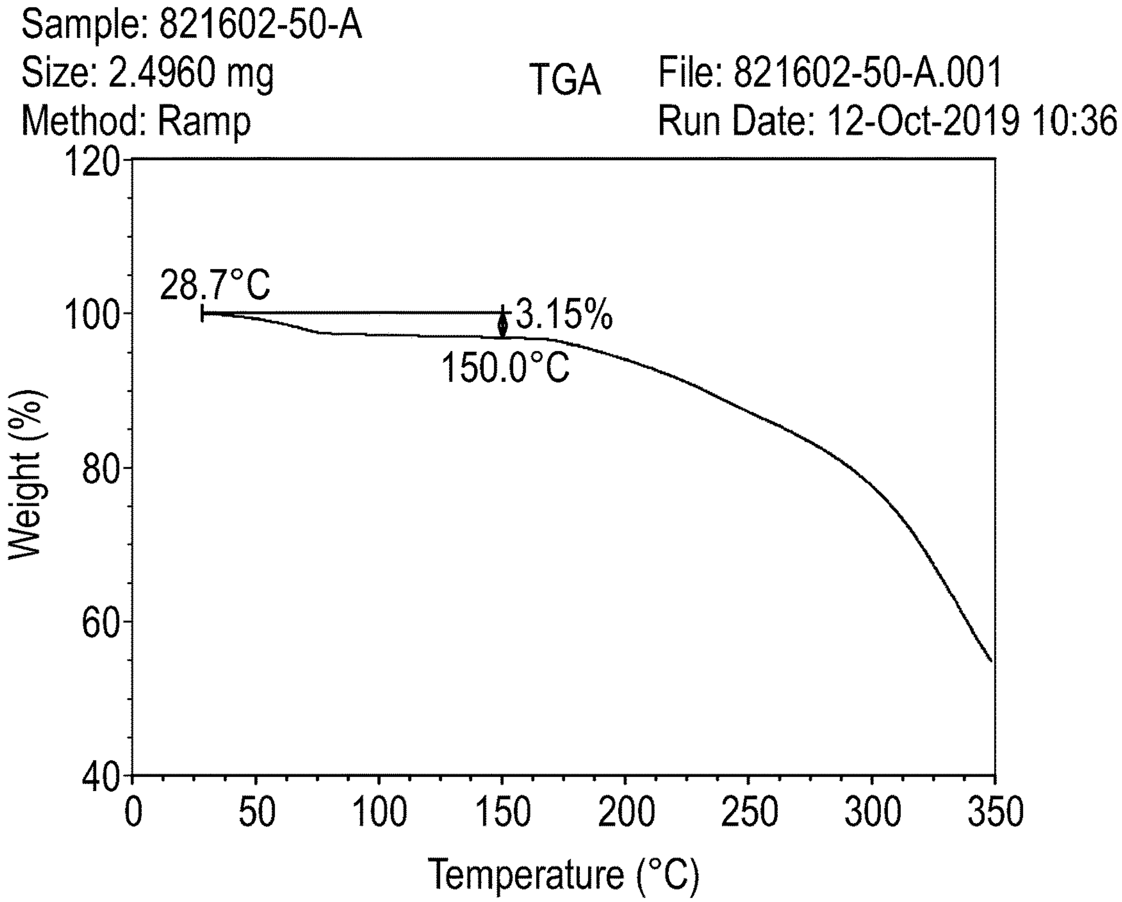
FIG. 2A shows the Thermogravimetric Analysis (TGA) thermogram of 1:1 Compound I Tris Salt (Form A).
Figure 2B:
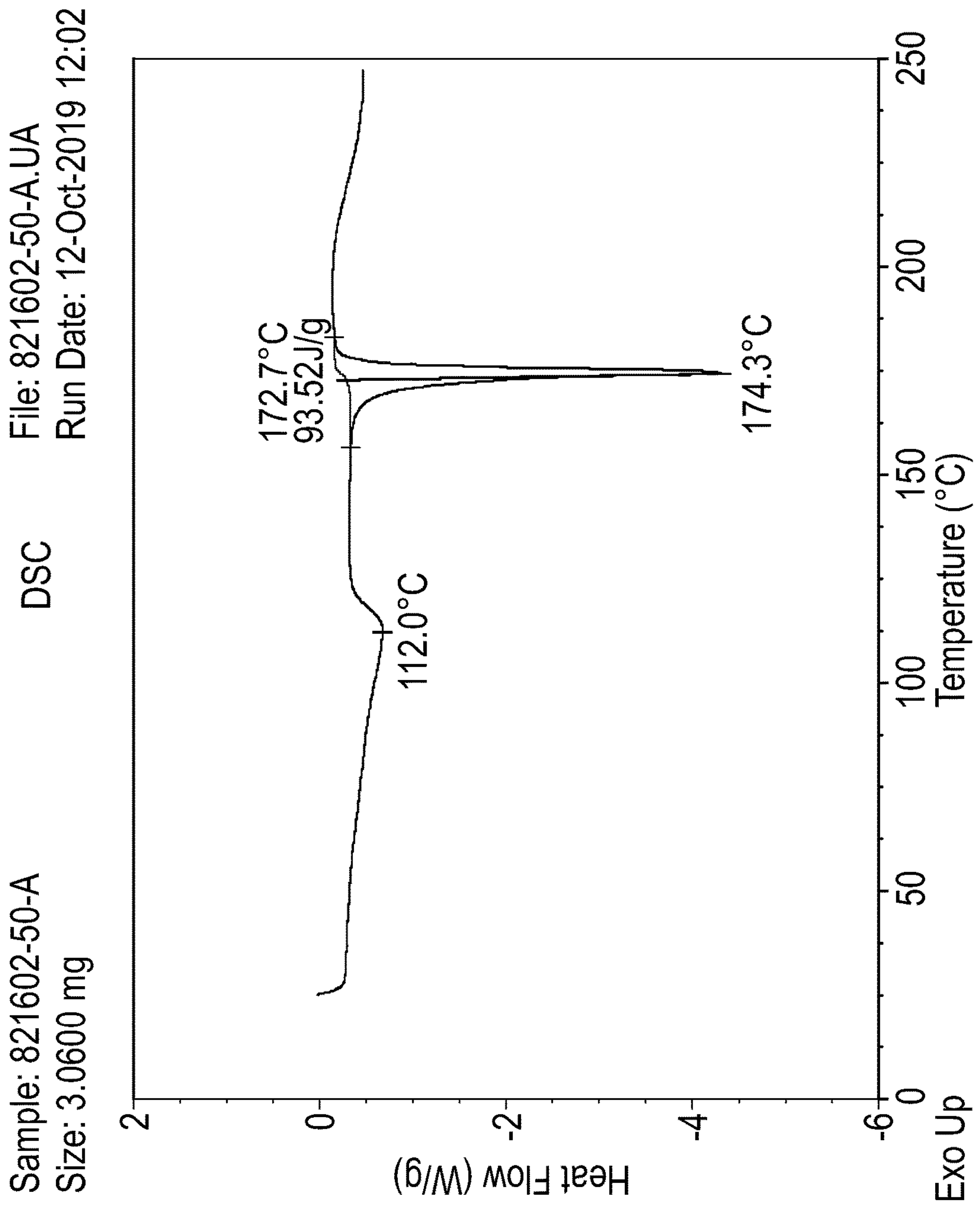
FIG. 2B shows the Differential Scanning calorimetry Analysis (DSC) thermogram of 1:1 Compound I Tris Salt (Form A).

The TGA results showed a weight loss of 3.2% up to 150° C. (FIG. 2A) and the DSC results showed two endotherms at 112.0° C. and 174.3° C. (peak temperature) (FIG. 2B).

The $^1$H NMR spectrum showed the molar ratio of tris/freeform was 1.0:1 and no residual solvent was observed. VH-XRPD and single crystal structure determination were performed for 1:1 Compound I Tris Salt (Form A) and it was identified as a monohydrate, which would dehydrate at the ≤30%RH condition. 1:1 Compound I Tris Salt (Form A) is thus suggested to be stored under the condition of 20-30° C. with relative humidity ≥40%RH to avoid dehydration.

TABLE 1

XRPD of 1:1 Compound 1 Tris Salt (Form A)

| Pos. [°2θ] | Height [cts] | FWHM Left [°2θ] | d-spacing [Å] | Rel. Int. [%] |
|---|---|---|---|---|
| 4.07 | 929.94 | 0.1023 | 21.73 | 52.01 |
| 8.06 | 555.58 | 0.1279 | 10.97 | 31.07 |
| 8.69 | 101.64 | 0.1535 | 10.17 | 5.68 |
| 9.63 | 426.90 | 0.1279 | 9.19 | 23.87 |
| 11.63 | 404.35 | 0.1279 | 7.61 | 22.61 |
| 12.09 | 345.47 | 0.1023 | 7.32 | 19.32 |
| 12.78 | 685.69 | 0.1279 | 6.93 | 38.35 |
| 13.87 | 128.86 | 0.3070 | 6.39 | 7.21 |
| 14.80 | 1020.11 | 0.1279 | 5.99 | 57.05 |
| 15.29 | 299.11 | 0.1023 | 5.80 | 16.73 |
| 16.13 | 512.32 | 0.1023 | 5.50 | 28.65 |
| 16.32 | 647.25 | 0.1535 | 5.43 | 36.20 |
| 17.45 | 1332.29 | 0.1023 | 5.08 | 74.51 |
| 18.78 | 970.22 | 0.1279 | 4.73 | 54.26 |
| 19.30 | 656.99 | 0.1279 | 4.60 | 36.74 |
| 20.09 | 1356.36 | 0.1023 | 4.42 | 75.86 |
| 20.70 | 1204.41 | 0.1279 | 4.29 | 67.36 |
| 21.11 | 1263.80 | 0.1023 | 4.21 | 70.68 |
| 21.88 | 222.18 | 0.1279 | 4.06 | 12.43 |
| 22.33 | 525.06 | 0.1023 | 3.98 | 29.36 |
| 22.61 | 1788.08 | 0.1535 | 3.93 | 100.00 |
| 23.34 | 307.78 | 0.1023 | 3.81 | 17.21 |
| 23.94 | 472.65 | 0.1279 | 3.72 | 26.43 |
| 25.07 | 606.43 | 0.1279 | 3.55 | 33.92 |
| 25.49 | 286.39 | 0.1023 | 3.49 | 16.02 |
| 25.80 | 561.56 | 0.1279 | 3.45 | 31.41 |
| 26.77 | 447.23 | 0.1279 | 3.33 | 25.01 |
| 27.72 | 452.04 | 0.1279 | 3.22 | 25.28 |
| 28.29 | 415.51 | 0.1535 | 3.15 | 23.24 |
| 29.24 | 90.66 | 0.2047 | 3.05 | 5.07 |
| 30.29 | 171.94 | 0.1535 | 2.95 | 9.62 |
| 31.68 | 197.27 | 0.1279 | 2.82 | 11.03 |
| 32.90 | 227.84 | 0.1535 | 2.72 | 12.74 |
| 34.32 | 136.46 | 0.1535 | 2.61 | 7.63 |
| 34.99 | 126.23 | 0.1535 | 2.56 | 7.06 |
| 36.78 | 48.24 | 0.3070 | 2.44 | 2.70 |
| 37.80 | 165.95 | 0.2047 | 2.38 | 9.28 |

3.1.2 Alternative Preparation Methods

The preparation of 1:1 Compound I Tris Salt (Form A) was attempted via slurry/solution crystallization for several times. The preparation results were summarized in Table A and Table B. The detailed characterization results were summarized in Table C.

TABLE A

Summary of re-preparation for 1:1 Compound 1 Tris Salt (Form A)

| Method | Solvent (v:v) | Anti-solvent | Solvent/Anti-solvent ratio | Scale (mg) | Result |
|---|---|---|---|---|---|
| Slurry | THF | — | — | 200 | Tris Salt Type A |
| | Acetone | — | — | 200 | Tris Salt Type A |
| Solution | Acetone/ | — | — | 15 | Tris Salt Type A |
| Crystallization | $H_2O$ | — | — | 500 | Tris Salt Type A |
| | (9:1) | — | — | 500 | Tris Salt Type A |
| | DMSO | IPA | 1:4 | 15 | No solid |
| | | Acetone | 1:2 | 15 | obtained |
| | | EtOAc | 1:4 | 15 | |
| | | Toluene | 1:2 | 15 | |

TABLE B

Summary of preparation procedures for 1:1 Compound I Tris Salt (Form A)

| Sample ID | Preparation procedure |
|---|---|
| 1 | 1. Weigh 299.8 mg Compound 1 freeform starting material and 64.7 mg Tris into a 20-mL vial, followed by addition of~10 mL THF to suspend the solids.<br>2. Stir (1000 rpm) at RT for~10 hrs, followed by stirring at 5° C. for~10 hrs, the sample became gel-like.<br>3. Stir at 50-5° C. (cycling at 0.1° C./min) for~12 hrs, the mixture was still gel-like.<br>4. Centrifuge (10000 rpm, 2 min) to isolate solids and vacuum dry the solids at RT for~2.5 days. |
| 2 | 1. Weigh 211.2 mg Compound 1 freeform starting material and 45.4 mg Tris into a 20-mL vial, followed by addition of~3 mL Acetone to suspend the solids.<br>2. Stir (1000 rpm) at RT for-4 hrs.<br>3. Transfer the sample to stir (1000 rpm) at 50-5° C. (cycling at 0.1° C./min) for~12 hrs, the mixture was still white suspension.<br>4. Centrifuge (10000 rpm, 2 min) to isolate solids and vacuum dry the solids at RT for 2 hrs. |
| 3 | 1. Dissolve~15 mg of Compound 1 free form in 0.7 mL Acetone/$H_2O$ (9:1, v:v) at 50 °C.<br>2. Dissolve equimolar Tris (3.3 mg) in 0.2 mL $H_2O$.<br>3. Add the Tris solution into freeform solution dropwise and stir at 50° C. (~1000 rpm), the sample was clear.<br>4. Continue stirring for 4 hours at RT, the sample was turbid.<br>5. Isolate the solids by centrifugation and vacuum dry at RT for 2 hours (~9 mg, yield ~50%). |
| 4 | 1. Dissolve 500.9 mg of freeform in 25 mL Acetone/$H_2O$ (9:1, v:v).<br>2. Dissolve equimolar Tris (108.2 mg) in 4 mL $H_2O$.<br>3. Add the Tris solution into freeform solution dropwise and stir at RT (~1000 rpm), the sample was turbid.<br>4. Continue stirring for 24 hours at RT, the sample was turbid.<br>5. Isolate the solids by centrifugation and vacuum dry at RT for 18 hours (381.7 mg, yield~62.7%). |
| 5 | 1. Dissolve 500.9 mg of freeform in 20 mL Acetone/$H_2O$ (9:1, v:v).<br>2. Dissolve equimolar Tris (107.9 mg) in 2.5 mL $H_2O$.<br>3. Add the Tris solution into freeform solution dropwise and stir at RT (~1000 rpm), the sample was turbid.<br>4. Continue stirring for 17 hours at RT, which was transferred to stir at 5° C. for 4 hours. The sample was turbid.<br>5. Isolate the solids by centrifugation and vacuum drying at RT for 20 hours (445.9 mg, yield ~73.2%). |

TABLE C

Summary of characterization results of re-prepared Tris Salt (Form A)

| Salt | Sample ID | Weight loss (%, 150° C.) | Endotherm (peak, ° C.) | Purity (area %) | Molar ratio (acid/base: freeform) |
|---|---|---|---|---|---|
| Tris salt | 1 | 7.1 | 89.4, 170.5 | 93.87 | 1.0:1 |
| Form A | 2 | 5.3 | 87.9, 169.0 | 95.46 | 1.0:1 |
| | 3 | 7.8 | 98.2, 174.6 | 97.46 | 1.0:1 |
| | 4 | 6.1 | 90.9, 174.2 | 98.04 | 0.9:1 |
| | 5 | 3.2 | 112.0, 174.3 | 98.16 | 1.0:1 |

Tris salt Form A (Sample ID 1) was re-prepared via slurry of equimolar freeform of Compound I and Tris in THF for 1 day, followed by vacuum drying at RT for —2.5 days.

While the crystallinity of the sample decreased significantly after vacuum drying. The TGA/DSC curves showed a weight loss of 7.1% up to 150° C. and two endotherms at 89.4° C. and 170.5° C. (peak temperature). The $^1$H NMR spectrum showed the molar ratio of Tris/freeform was 1.0:1 and the molar ratio of residual THF/freeform was 0.62:1 (6.1%, wt %). The HPLC purity of Tris salt Form A (Sample ID 1) was measured to be 93.87 area %.

Tris salt Form A (Sample ID 3) was obtained via solution crystallization using 15 mg freeform and equalmolar Tris as starting material. The TGA/DSC curves showed a weight loss of 7.8% up to 150° C. and two endotherms at 98.2° C. and 174.6° C. (peak temperature). The $^1$H NMR spectrum indicated the molar ratio of Tris/freeform was 1.0:1, and the molar ratio of residual Acetone/freeform was 0.04:1 (0.3%, wt %). The HPLC purity of Tris salt Form A (Sample ID 3) was measured to be 97.46 area %.

Tris salt Form A (Sample ID 4) was obtained via solution crystallization using 500 mg freeform and equalmolar Tris as starting material. The TGA/DSC curves showed a weight loss of 6.1% up to 150° C. and two endotherms at 90.9° C. and 174.2° C. (peak temperature). The $^1$H NMR spectrum indicated the molar ratio of Tris/freeform was 0.9:1, and the molar ratio of residual Acetone/freeform was 0.04:1 (0.3%, wt %). The HPLC purity of Tris salt Form A (Sample ID 4) was measured to be 98.04 area %. This batch of sample was not further used for formulation study since the molar ratio was not 1:1.

Tris salt Form A (Sample ID 5) was obtained via solution crystallization using 500 mg freeform and equalmolar Tris as starting material. The TGA/DSC curves showed a weight loss of 3.2% up to 150° C. and two endotherms at 112.0° C. and 174.3° C. (peak temperature). The $^1$H NMR spectrum indicated the molar ratio of Tris/freeform was 1.0:1, and the molar ratio of residual Acetone/freeform was 0.05:1 (0.4%, wt %). The HPLC purity of Tris salt Form A (Sample ID 5) was measured to be 98.16 area %.

3.2 Single Crystal Growth

The single crystal sample of 1:1 Compound I Tris Salt (Form A), characterized by SCXRD, was obtained from a slow evaporation experiment. The experiment details are elaborated below.

15.0 mg 1:1 Compound I Tris Salt (Form A) starting material was added into a 3-mL glass vial with the addition of 1.0 mL ACN/MeOH (1:1, v:v) solvent mixture. After being shaken by ultrasonic cleaner to accelerate dissolution, the suspension was filtered. The obtained clear solution was transferred to a clean 4-mL shell vial. The shell vial was sealed by PE-Plug with one pinhole on it. Then it was placed in fume hood at room temperature for slow evaporation. After 2 days' slow evaporation, rod-like crystals were observed.

Figure 3:
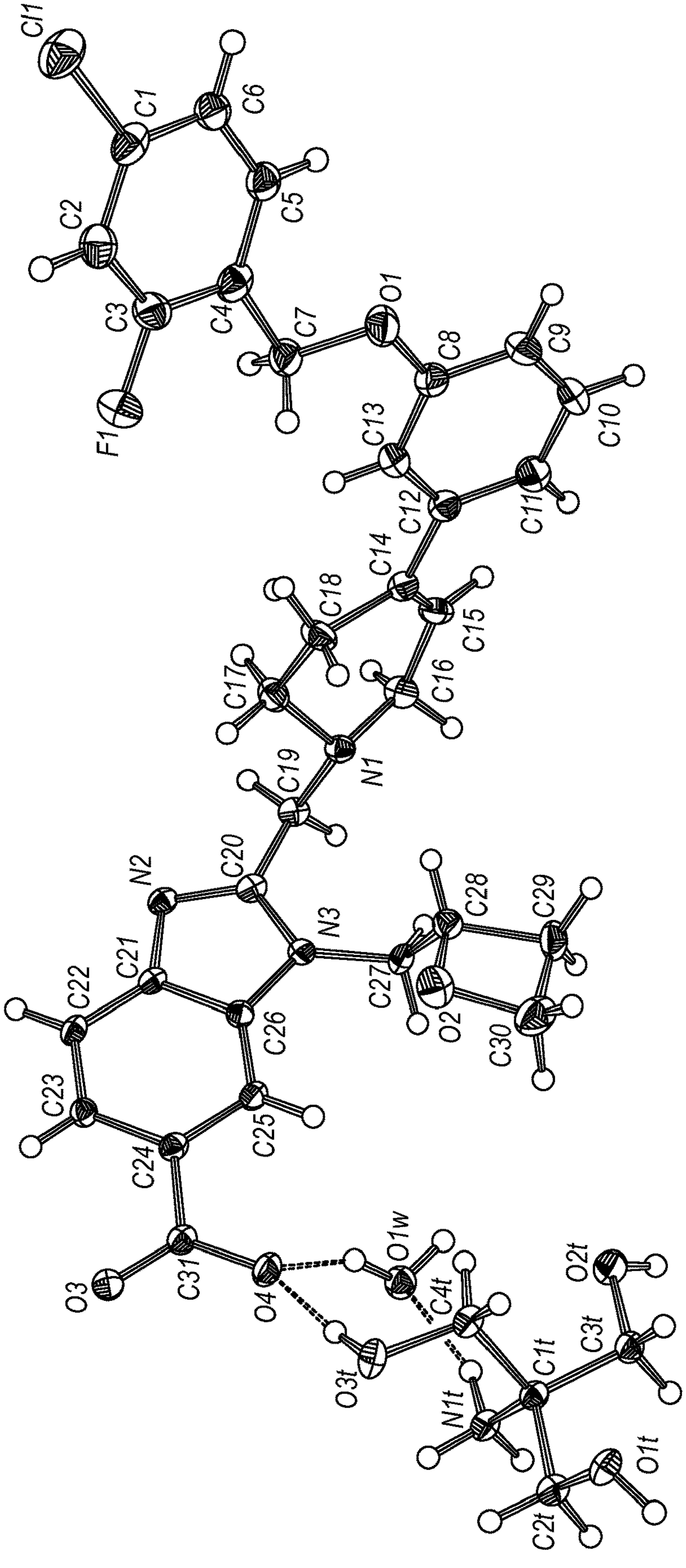
FIG. 3 shows the Single Crystal X-Ray Diffraction (SCXRD) pattern of 1:1 Compound I Tris Salt (Form A).

As evidenced in single crystal X-ray crystallography (FIG. 3), the asymmetric unit of the Type A single crystal structure is comprised of one Compound I anion, one tris cation and one water molecule, which confirms that the Form A is a monohydrate of 1:1 Compound I tris salt.

3.3 Kinetic Solubility

I) Preparation of Bio-Relevant Media and pH Buffers

Simulated Gastric Fluid (SGF)

Weigh 100 mg of sodium chloride and 50 mg of Triton X-100 into a 50-mL volumetric flask. Add appropriate volume of purified water and sonicate until all solids are completely dissolved. Add about 68 μL of 12 M HCl and sufficient purified water closely to the target volume and adjust to pH 1.8. Dilute to volume with purified water, mix well and check the pH with a pH meter.

Fasted-State Simulated Intestinal Fluid (FaSSIF)

Weigh 170 mg of sodium phosphate monobasic, 21 mg of sodium hydroxide and 310 mg of sodium chloride, 110 mg of SIF powder into a 50-mL volumetric flask. Add appropriate volume of purified water and sonicate until all solids are completely dissolved. Add sufficient purified water closely to the target volume and adjust to pH 6.5. Dilute to volume with purified water, mix well and check the pH with a pH meter.

Fed-State Simulated Intestinal Fluid (FeSSIF)

Weigh 0.41 mL of glacial acetic acid, 202 mg of sodium hydroxide and 594 mg of sodium chloride, 560 mg of SIF powder into a 50-mL volumetric flask. Add appropriate volume of purified water to dissolve the solids. Then add sufficient purified water closely to the target volume and adjust to pH 5.0. Dilute to volume with purified water, mix well and check the pH with a pH meter.

pH 8.0 Buffer

Weight 302.5 mg of Tris into a 50-mL volumetric flask. Add sufficient purified water closely to the target volume and adjust to pH 8.0. Dilute to volume with purified water, mix well and check the pH with a pH meter.

II) Kinetic Solubility Test

Kinetic solubility was evaluated in water and three bio-relevant media (SGF, FaSSIF and FeSSIF) for 1/4/24 hours. 3-4 mg of solids were suspended in 3 mL each medium (solid loading: 1 mg/mL, calculated using freeform) to get a suspension, followed by rolling (25 rpm) at 37° C. for 1/4/24 hours. At each time point, ~1.0 mL of suspension was sampled out for centrifugation (12000 rpm, 2 min) and filtration through 0.45 μm PTFE membrane to obtain supernatant for HPLC and pH tests, the residual solids were analyzed by XRPD. Detailed results were summarized in Table 2.

Based on the results of solubility evaluation, 1:1 Compound I Tris Salt (Form A) showed better solubility in $H_2O$. Freeform and Tris salt Type A showed similar solubility in FaSSIF and FeSSIF after 1 hour. Form change was observed for 1:1 Compound I Tris Salt (Form A) in SGF and the XRPD results after solubility test. The purity decrease was for reference only since the samples were suspensions.

TABLE 2

Summary of kinetic solubility test

| Material | Media | 1 hour* | | | | 4 hours* | | | | 24 hours# | | | |
|---|---|---|---|---|---|---|---|---|---|---|---|---|---|
| | | S | pH | FC | Purity (%)^ | S | pH | FC | Purity (%)^ | S | pH | FC | Purity (%)^ |
| Tris salt Form A | $H_2O$ | 0.1 | 8.0 | No | 96.74 | 0.1 | 8.2 | No | 89.77 | 0.05 | 8.4 | No | 60.35 |
| | FaSSIF | 0.2 | 6.5 | No | 92.63 | 0.01 | 6.6 | No | 49.59 | 0.01 | 6.6 | No | 58.70 |
| | FeSSIF | 0.5 | 5.1 | No | 94.61 | 0.2 | 5.0 | No | 81.75 | 0.03 | 5.0 | No | 43.32 |
| | SGF | 0.4 | 1.9 | Yes | 93.12 | 0.4 | 2.0 | Yes | 93.05 | 0.5 | 1.9 | Yes | 89.49 |
| Free form amorphous | $H_2O$ | 0.03 | 8.4 | No | 100.00 | 0.02 | 7.3 | No | 87.13 | <LOQ | 6.8 | No | 9.97 |
| | FaSSIF | 0.2 | 6.5 | No | 93.54 | 0.08 | 6.5 | No | 49.59 | 0.04 | 6.4 | Yes | 63.24 |
| | FeSSIF | 0.4 | 5.0 | No | 94.78 | 0.5 | 5.0 | No | 91.80 | 0.4 | 5.0 | No | 77.57 |
| | SGF | 0.4 | 1.9 | No | 93.07 | 0.6 | 1.9 | No | 94.02 | 0.8 | 1.9 | No | 91.48 |

S: solubility (mg/mL), calculated using freeform.

FC: form change.

*LOQ = 0.16 μg/mL, HOQ = 190.6 μg/mL;

#LOQ = 0.15 μg/mL, HOQ = 190.6 μg/mL;

^Area percentage of API (calculated by area normalization method). The data was for reference only since the samples were suspensions.

NA: The sample was insufficient for XRPD test.

3.4.1 Solid Stability Evaluation (I/II)

To evaluate the physical and chemical stability of 1:1 Compound I Tris Salt (Form A) and amorphous free form, samples were stored under the conditions of 60° C. for 1 day and 25° C./60% RH or 40° C./75% RH for 1 week, respectively. The solids were characterized using XRPD and HPLC, and the results were summarized in Table Table 3. No form change was observed after one week. 1:1 Compound I Tris Salt (Form A) showed better chemical stability in all conditions than the amorphous free form.

TABLE 3

Summary of solid stability evaluation (I/II)

| Starting material | Experimental condition | Sampling time | Observation | Form change | Purity *(area %) |
|---|---|---|---|---|---|
| Tris salt Form A | Initial | — | White powder | No | 95.46 |
| | 60° C. (capped) | 1 day | Yellowish powder | No | 93.49 |
| | 25° C./60% RH (open) | 1 week | Yellowish powder | No | 94.70 |
| | 40° C./75% RH (open) | 1 week | Yellowish powder | No | 95.40 |
| Amorphous Free form | Initial | — | White powder | No | 94.71 |
| | 60° C. (capped) | 1 day | Yellowish powder | No | 86.88 |
| | 25° C./60% RH (open) | 1 week | Yellowish powder | No | 93.06 |
| | 40° C./75% RH (open) | 1 week | Yellowish powder | No | 89.59 |

*Area percentage of API (calculated with area normalization method).

3.4.2 Solid Stability Evaluation (II/II)

The chemical stability of 1:1 Compound I Tris Salt (Form A) was further evaluated at solid state, samples were stored under the ambient condition or 40° C./75% RH for 1 day and 3 days, respectively. The HPLC purity and weight purity were tested using HPLC in triplicate, and the results were summarized in Table 4. 1:1 Compound I Tris Salt (Form A) showed better chemical stability in all conditions.

TABLE

Error! No text of specified style in document.
Summary of solid stability evaluation (II/II)

| Material | Experimental condition | Sampling time | Ave. Purity* (area%) | CV** (%) |
|---|---|---|---|---|
| Tris salt Form A | Initial | — | 94.5 | 0.3 |
| | Ambient condition (open) | 1 day | 94.8 | 0.6 |
| | | 3 days | 94.8 | 0.2 |
| | 40° C./75% RH (open) | 1 day | 94.8 | 0.4 |
| | | 3 days | 94.7 | 0.3 |

*Tested using HPLC in triplicate, calculated by average.
**Control variable

3.5 Solution Stability Evaluation

Solution stability in SGF (pH 1.8) and pH 8.0 buffer was evaluated for 1:1 Compound I Tris Salt (Form A) at RT. Clear solutions were prepared at the concentration of 0.01 mg/mL and then placed at RT for 6 hours, 1 and 5 days. No significant degradation was observed for the pH 1.8 solution after 1 day, while the purity of the pH 8.0 solution decreased slightly. The HPLC purity and pH value were summarized in Table 5 and Table 6.

TABLE 5

Summary of solution stability evaluation for 1:1 Compound 1 Tris Salt (Form A) I/II

| | | Initial | | 6 hours | | |
|---|---|---|---|---|---|---|
| Concentration | Media | Purity (% area) | pH | Purity (%area) | Purity vs. Initial (%) | pH |
| 0.01 mg/mL | pH 1.8 (SGF) | 100.00 | 1.8 | 100.00 | 100.0 | 1.8 |
| | pH 8.0 (50 mM phosphate) | 97.70 | 8.1 | 96.92 | 99.2 | 8.0 |

TABLE 6

Summary of solution stability evaluation for 1:1 Compound I Tris Salt (Form A) II/II

| | | 1 day | | | 5 days | | |
|---|---|---|---|---|---|---|---|
| Concentration | Media | Purity (% area) | Purity vs. Initial (%) | pH | Purity (% area) | Purity vs. Initial (%) | pH |
| 0.01 mg/mL | pH 1.8 (SGF) | 100.00 | 100.0 | 1.8 | 97.40 | 97.4 | 1.8 |
| | pH 8.0 (50 mM phosphate) | 96.07 | 98.3 | 8.0 | 94.34 | 96.6 | 8.0 |

3.6 Hygroscopicity

To investigate the solid form stability as a function of humidity, DVS isotherm plot of 1:1 Compound I Tris Salt (Form A) was collected between 0% RH and 95% RH at 25° C. A water uptake of 2.77% was observed at 25° C./80% RH. Considering the 1:1 Compound I Tris Salt (Form A) is a hydrate and may dehydrate under low humidity, DVS was also tested at 20 and 30° C. to further confirm the suitable storage condition and avoid dehydration. Detailed results were summarized in Table 7. No form change was observed after DVS test. Combing the VH-XRPD and DVS results: the condition of 20-30° C. and relative humidity ≥40% RH is suitable for the storage of 1:1 Compound I Tris Salt (Form A).

TABLE 7

Summary of DVS test

| Salt | Temperature | Water uptake (80% RH) | Hygroscopicity[1] | Form change after DVS test |
|---|---|---|---|---|
| Tris salt Form A | 20° C. | 2.24 | Hygroscopic | No |
| | 25° C. | 2.77 | Hygroscopic | No |
| | 30° C. | 2.99 | Hygroscopic | No |

[1]According to Chinese Pharmacopeia 2015

3.7 Polymorph Screening

Polymorph screening experiments on 1:1 Compound I Tris Salt (Form A) were performed under vairous conditions using different solution crystallization or solid transition methods, including anti-solvent addition, reverse anti-solvent addition, slow evaporation, slow cooling, slurry at RT, slurry at 50° C., slurry cycling 5-50° C., vapor-solid diffusion, vapor-solution diffusion, polymer induced crystallization, and grinding.

The screeing results show that 1:1 Compound I Tris Salt (Form A) did not change under most of the test conditions, indicating that Form A is stable.

EXAMPLE 4

Preparations and Characterization of Crystalline Form of 1:1 Compound II Citrate Salt (Form A)

4.1.1 Preparation Method 15 mg of free form of Compound II and 5.21 mg of citric acid in acetone were mixed. The obtained slurry was stirred at RT for 3 days, followed by vacuum drying at RT for ~12 hrs.

Figure 4:
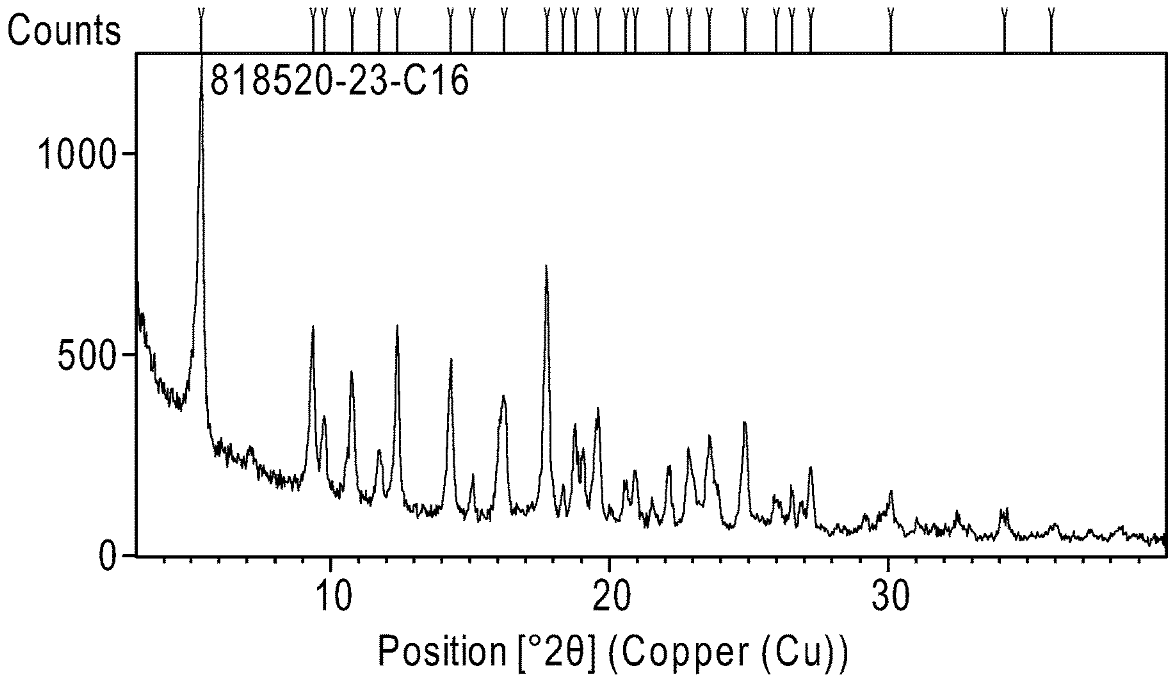
FIG. 4 shows the X-ray Powder Diffraction (XRPD) pattern of 1:1 Compound II Citrate Salt (Form A).
Figure 5A:
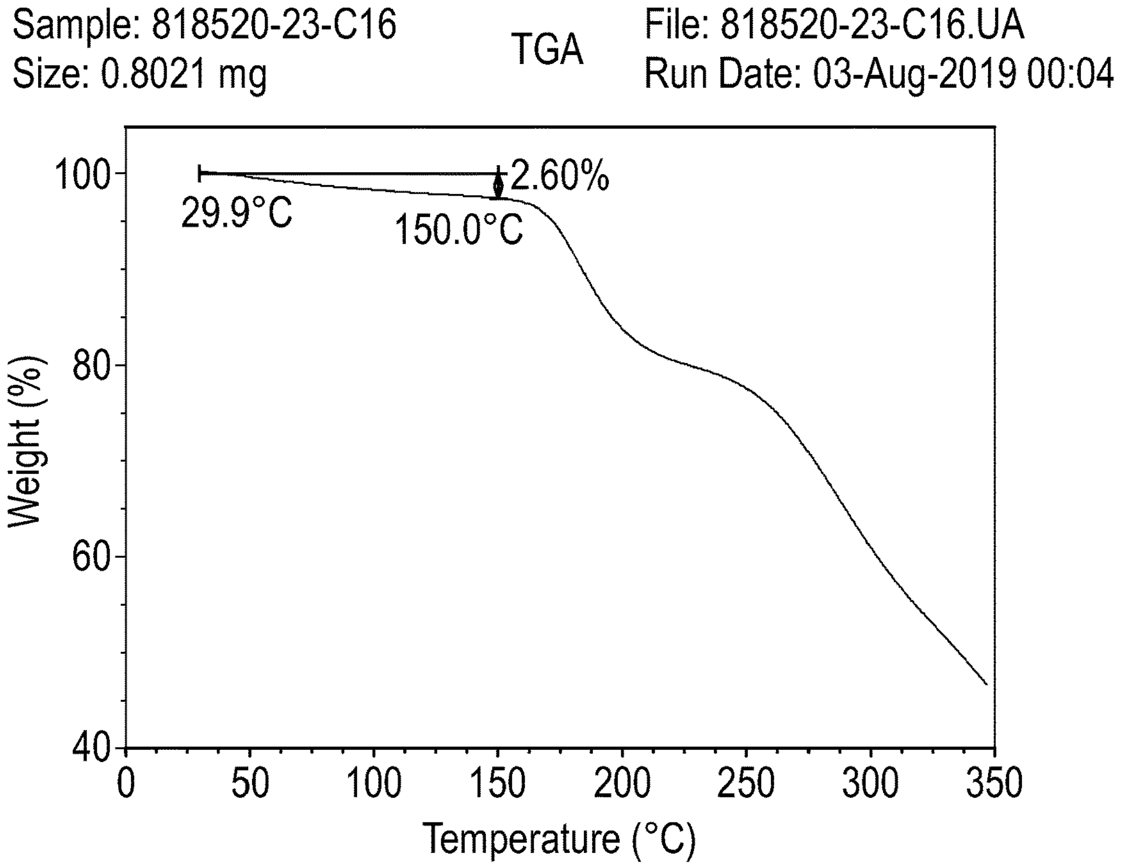
FIG. 5A shows the Thermogravimetric Analysis (TGA) thermogram of 1:1 Compound II Citrate Salt (Form A).
Figure 5B:
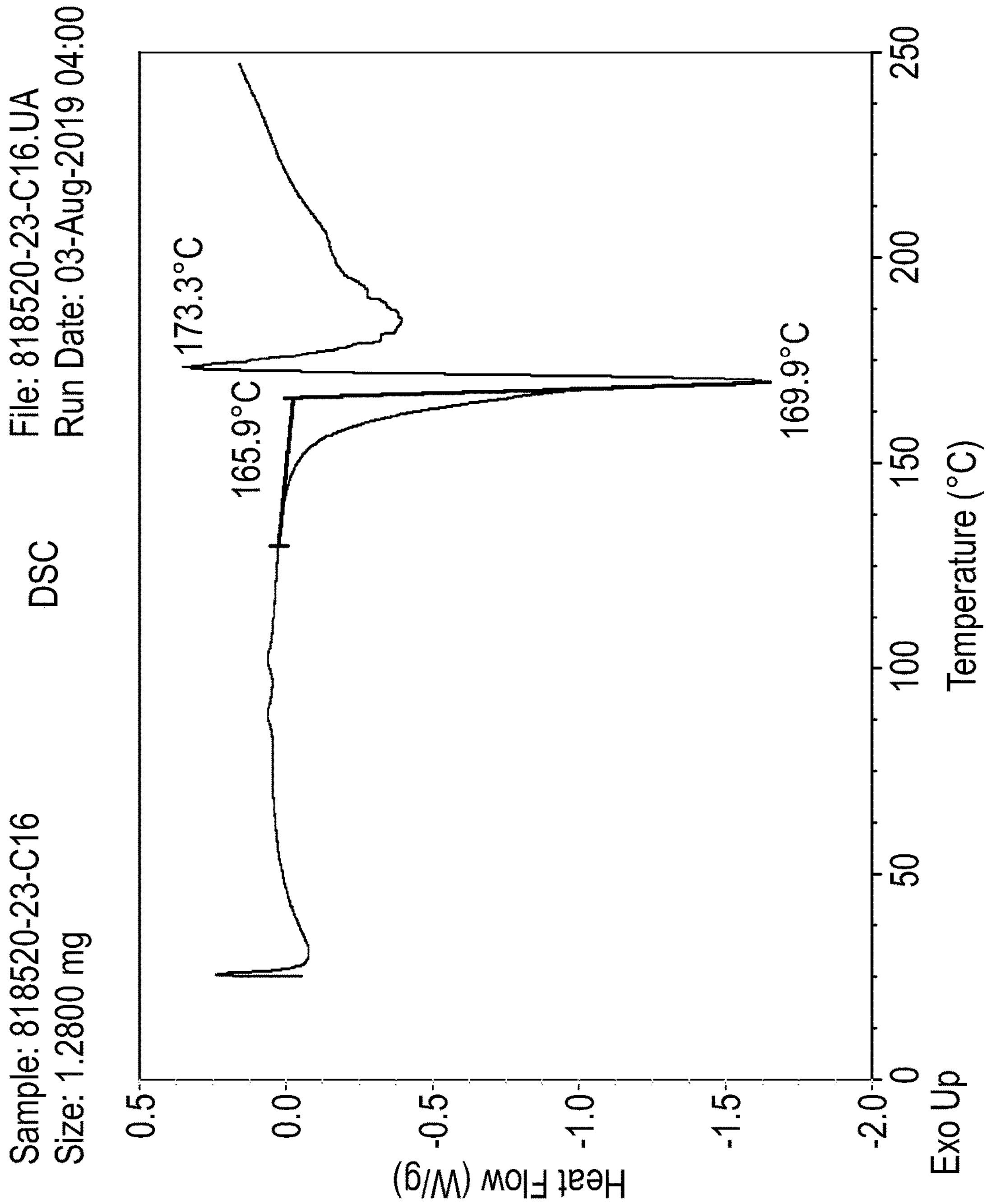
FIG. 5B shows the Differential Scanning calorimetry Analysis (DSC) thermogram of 1:1 Compound II Citrate Salt (Form A).

The solid obtained was further characterized by XRPD (FIG. 4 and Table 8). The TGA (FIG. 5A) results showed a weight loss of 2.6% up to 150° C. and the DSC results (FIG. 5B) showed one endotherm at 169.9° C. ° C. and one exotherm at 173.3° C. (peak temperature).

TABLE 8

| XRPD of 1:1 Compound II Citrate Salt (Form A) | | | | |
|---|---|---|---|---|
| Pos. [°2θ] | Height [cts] | FWHM Left [°2θ] | d-spacing [Å] | Rel. Int. [%] |
| 5.37 | 930.24 | 0.1535 | 16.46 | 100.00 |
| 9.35 | 400.05 | 0.1279 | 9.46 | 43.01 |
| 9.76 | 182.67 | 0.1535 | 9.06 | 19.64 |
| 10.76 | 289.65 | 0.1279 | 8.22 | 31.14 |
| 11.75 | 125.33 | 0.2047 | 7.53 | 13.47 |
| 12.39 | 448.33 | 0.1023 | 7.14 | 48.20 |
| 14.31 | 382.17 | 0.1791 | 6.19 | 41.08 |
| 15.09 | 84.69 | 0.1535 | 5.87 | 9.10 |
| 16.24 | 289.92 | 0.1791 | 5.46 | 31.17 |

TABLE 8-continued

| XRPD of 1:1 Compound II Citrate Salt (Form A) | | | | |
|---|---|---|---|---|
| Pos. [°2θ] | Height [cts] | FWHM Left [°2θ] | d-spacing [Å] | Rel. Int. [%] |
| 17.77 | 614.43 | 0.1791 | 4.99 | 66.05 |
| 18.33 | 72.53 | 0.1535 | 4.84 | 7.80 |
| 18.76 | 236.58 | 0.1535 | 4.73 | 25.43 |
| 19.59 | 276.86 | 0.1279 | 4.53 | 29.76 |
| 20.58 | 92.61 | 0.1535 | 4.31 | 9.96 |
| 20.93 | 126.48 | 0.1535 | 4.24 | 13.60 |
| 22.15 | 119.95 | 0.1791 | 4.01 | 12.89 |
| 22.88 | 177.85 | 0.2047 | 3.89 | 19.12 |
| 23.61 | 219.48 | 0.2047 | 3.77 | 23.59 |
| 24.88 | 258.51 | 0.1535 | 3.58 | 27.79 |
| 26.00 | 67.98 | 0.2558 | 3.43 | 7.31 |
| 26.56 | 84.29 | 0.1279 | 3.36 | 9.06 |
| 27.24 | 155.13 | 0.1535 | 3.27 | 16.68 |
| 30.08 | 97.91 | 0.2047 | 2.97 | 10.53 |
| 34.19 | 50.14 | 0.3070 | 2.62 | 5.39 |
| 35.89 | 24.20 | 0.6140 | 2.50 | 2.60 |

4.1.2 Alternative Preparation Methods

The preparation of 1:1 Compound II Citrate Salt (Form A) was attempted via slurry/solution crystallization for several times. The preparation results were summarized in Table 9 and Table 10. The detailed characterization results were summarized in Table 11.

TABLE 9

| Summary of re-preparation for 1:1 Compound II Citrate Salt (Form A) | | | | | |
|---|---|---|---|---|---|
| Method | Solvent (v:v) | Anti-solvent | Solvent/Anti-solvent ratio | Scale (mg) | Result |
| Slurry | Acetone | — | — | 300 | Citrate salt Form A |
| Solution Crystallization | Acetone | — | — | 15 | Citrate salt Form A |
| | Acetone | — | — | 500 | Citrate salt Form A |
| | Acetone | n-heptane | 1:2 | 15 | Gel-like |

TABLE 10

| Summary of preparation procedures for 1:1 Compound II Citrate Salt (Form A) | |
|---|---|
| Sample ID | Preparation procedure |
| 1 | 1. Weigh 302.4 mg Compound II freeform starting material and 104.3 mg citric acid into a 20-mL vial, followed by addition of~10 mL Acetone to suspend the solids.<br>2. Stir (1000 rpm) at RT for 1 day.<br>3. Centrifuge (10000 rpm, 2 min) to isolate solids and vacuum dry the solids at RT for~1.5 days. |
| 2 | 1. Dissolve~15 mg of freeform in 0.3 mL Acetone.<br>2. Dissolve equimolar citric acid (5.2 mg) in 0.2 mL Acetone.<br>3. Add the acid solution into freeform solution dropwise and stir at RT (~1000 rpm), the sample was clear.<br>4. Continue stirring for 13 hours at RT, the sample was turbid.<br>5. Isolate the solids by centrifugation. (~14 mg, yield ~75%). |
| 3 | 1. Dissolve~500 mg of freeform in 12 mL Acetone.<br>2. Dissolve equimolar citric acid (173.6 mg) in 4 mL Acetone.<br>3. Add the acid solution into freeform solution dropwise and stir at RT (~1000 rpm), the sample was clear.<br>4. Continue stirring for 2 days at RT, the sample was turbid.<br>5. Isolate the solids by centrifugation. (~506.3 mg, yield~75%). |

TABLE 11

| Summary of characterization results of 1:1 Compound II Citrate Salt (Form A) | | | | | |
|---|---|---|---|---|---|
| Salt | Sample ID | Weight loss (%, 150° C.) | Endotherm (peak, ° C.) | Purity (area %) | Molar ratio (acid/base: freeform) |
| Citrate Form A | 1 | 1.4 | 171.9, 175.5* | 97.73 | 1.0:1 |
| | 2 | 3.1 | 169.9, 173.6* | 97.05 | 1.0:1 |
| | 3 | 2.5 | 166.6, 171.0* | 96.66 | 1.0:1 |

*Exotherm.

1:1 Compound II Citrate Salt (Form A) (Sample ID 1) was re-prepared via slurry of equimolar starting material and citric acid in Acetone for 1 day, followed by vacuum drying at RT for ~1.5 days. The TGA/DSC curves showed a weight loss of 1.4% up to 150° C., one endotherm at 171.9° C. and one exotherm at 175.5° C. (peak temperature). The $^1$H NMR spectrum showed the molar ratio of citric acid/freeform was 1.0:1 (the NMR signals of citric acid and freeform overlapped, and the integral of freeform was deducted for calculation), and the molar ratio of residual Acetone/freeform was 0.16:1 (1.2%, wt %). The HPLC purity of 1:1 Compound II Citrate Salt (Form A) (Sample ID 1) was measured to be 97.73 area %.

1:1 Compound II Citrate Salt (Form A) (Sample ID 2) was obtained via solution crystallization using 15 mg freeform and citric acid (molar ratio of 1:1, acid/freeform) as starting material. The TGA/DSC curves showed a weight loss of 3.1% up to 150° C. and one endotherm at 169.9° C. and one exotherm at 173.6° C. (peak temperature). The $^1$H NMR spectrum indicated the molar ratio of citric acid/freeform was 1.0:1 (the integral of freeform was deducted for calculation), and the molar ratio of residual Acetone/freeform was 0.09:1 (0.9%, wt %). The HPLC purity of 1:1 Compound II Citrate Salt (Form A) (Sample ID 2) was measured to be 97.05 area %.

1:1 Compound II Citrate Salt (Form A) (Sample ID 3) was obtained via solution crystallization using 500 mg freeform and citric acid (molar ratio of 1:1, acid/freeform) as starting material. The TGA/DSC curves showed a weight loss of 2.5% up to 150° C. and one endotherm at 166.6° C. and one exotherm at 171.0° C. (peak temperature). The $^1$H NMR spectrum indicated the molar ratio of citric acid/freeform was 1.0:1 (the integral of freeform was deducted for calculation), and the molar ratio of residual Acetone/freeform was 0.08:1 (0.6%, wt %). The HPLC purity of 1:1 Compound II Citrate Salt (Form A) (Sample ID 3) was measured to be 96.66 area %.

EXAMPLE 5

Preparations and Characterization of Crystalline Form of 1:1 Compound II Tris Salt (Form B)

5.1.1 Preparation Methods

Batch A

1) Under $N_2$ atmosphere, a reactor was charged with acetone (10 L, 10.0V). 1.0 Kg of free form of Compound II (1.0 eq) were add to the reactor with agitation. The temperature was adjusted to 23° C., and the obtained mixture was stirred for 0.5 hour before the mixture was filtered with 0.2 μm microporous filter. The filtrate was collected.

2) Under $N_2$ atmosphere, the filtrate was transferred to the reactor. 10 L of EA (10.0V) were added to the reactor. The temperature was adjusted to 21° C. A Tris solution (218.8 g of Tris (1.0eq) dissolved in 2 L of soften water (2.0V)) was added to the reactor within 1.5 hours. The mixture was stirred for 1 hour.

3) The mixture was then isolated by centrifuge. The cake was washed with EA (2 L, 2.0V) and the filter cake was collected.

4) The filter cake was dried under vacuum at 70° C. for 16 hours to obtain 1.03 Kg of 1:1 Compound II Tris Salt (Form B) as off-white solid.

Batch B

1) Under $N_2$ atmosphere, a reactor was charged with acetone (21.5 L, 10.0V). 2.15 Kg of free form of Compound II (1.0 eq) were add to the reactor with agitation. The temperature was adjusted to 25° C., and the obtained mixture was stirred for 0.5 hour before the mixture was filtered with 0.2 μm microporous filter. The filtrate was collected.

2) Under $N_2$ atmosphere, the filtrate was transferred to the reactor. 21.5 L of EA (10.0V) were added to the reactor. The temperature was adjusted to 21° C. A Tris solution (470.4 g of Tris (1.0 eq) dissolved in 4.3 L of soften water (2.0V)) was added to the reactor within 3 hours. The mixture was stirred for 1.5 hours.

3) The mixture was then isolated by centrifuge. The cake was washed with EA (4.3 L, 2.0V) and the filter cake was collected.

4) The filter cake was dried under vacuum at 70° C. for 16 hours to obtain 2.45 Kg of 1:1 Compound II Tris Salt (Form B) as white solid.

Batch C 1) 3.45 Kg (1.0eq) of 1:1 Compound II Tris Salt (Form B) obtained from Batch A and Batch B were mixed with 3.45 L of soften water (1V). The mixture was added to a reactor charged with 44.9 L of EA (13V) under $N_2$ atmosphere with agitation. The temperature was adjusted to 25° C., and the obtained mixture was stirred for 1 hour.

2) The mixture was then isolated by centrifuge. The cake was washed with EA (6.9 L, 2.0V) and the filter cake was collected.

3) The filter cake was dried under vacuum at 70° C. for 16 hours to obtain 3.45 Kg of 1:1 Compound II Tris Salt (Form B) as off-white solid.

Figure 6:
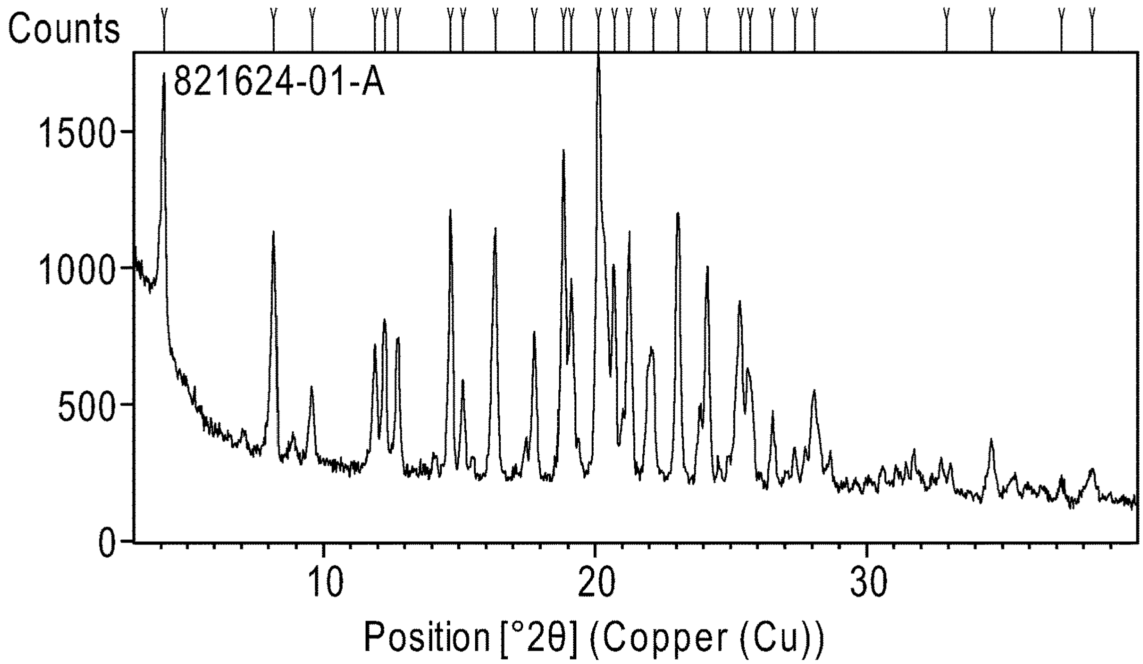
FIG. 6 shows the X-ray Powder Diffraction (XRPD) pattern of 1:1 Compound II Tris Salt (Form B).
Figure 7A:
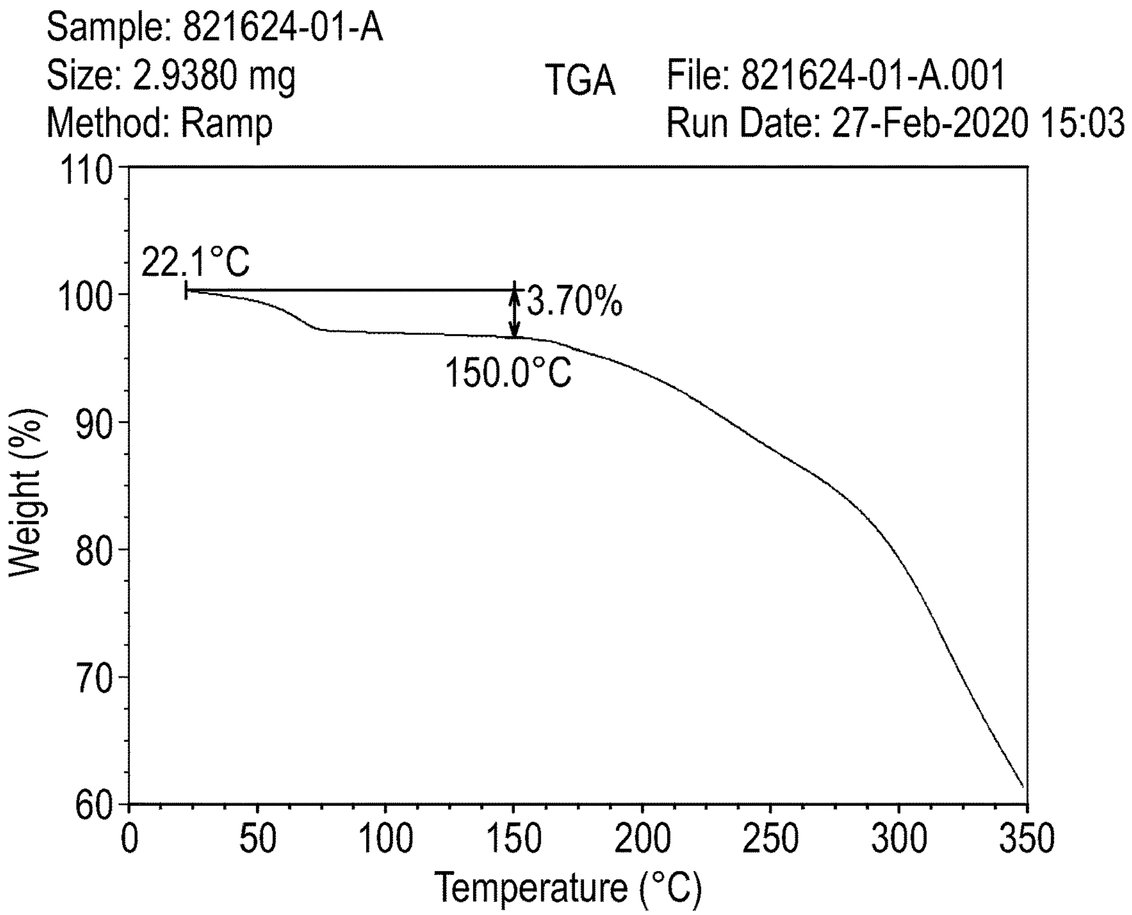
FIG. 7A shows the Thermogravimetric Analysis (TGA) thermogram of 1:1 Compound II Tris Salt (Form B).
Figure 7B:
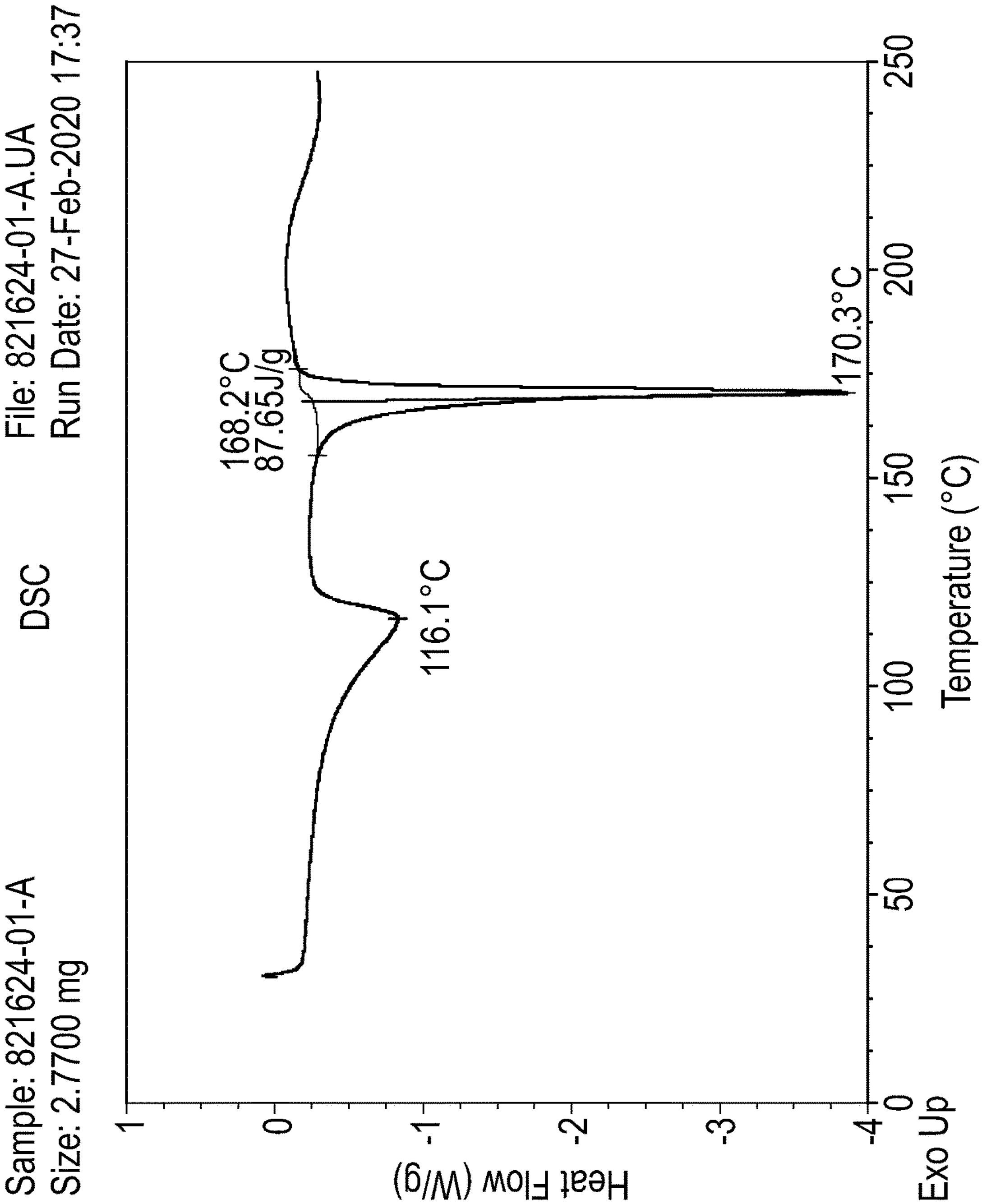
FIG. 7B shows the Differential Scanning calorimetry Analysis (DSC) thermogram of 1:1 Compound II Tris Salt (Form B).

1:1 Compound II tris salt (Form B) of Batch C was characterized by XRPD (FIG. 6 and Table 5-1). The TGA results showed a weight loss of 3.7% up to 150° C. (FIG. 7A) and the DSC results (FIG. 7B) showed two endotherms at 116.1° C. and 170.3° C. (peak temperature).

VH-XRPD was performed for a 1:1 Compound II tris salt (Form B) sample for further identification. The VH-XRPD indicated that the tris salt Form B converted to a new form at 10% RH with $N_2$, which converted back after being exposed at ambient condition (40% RH). Combining the characterization results, it is believe that 1:1 Compound II tris salt (Form B) is a hydrate, which would dehydrate below ≤10% RH.

TABLE 5-1

XRPD of 1:1 Compound II Tris Salt (Form B)

| Pos. [°2θ] | Height [cts] | FWHM Left [°2θ] | d-spacing [Å] | Rel. Int. [%] |
|---|---|---|---|---|
| 4.14 | 1210.22 | 0.1279 | 21.33 | 78.09 |
| 8.18 | 793.52 | 0.1535 | 10.81 | 51.20 |
| 9.57 | 267.23 | 0.1535 | 9.24 | 17.24 |
| 11.91 | 454.86 | 0.1535 | 7.43 | 29.35 |
| 12.27 | 535.56 | 0.1279 | 7.21 | 34.56 |
| 12.75 | 479.45 | 0.1535 | 6.94 | 30.94 |
| 14.69 | 959.67 | 0.1279 | 6.03 | 61.92 |
| 15.13 | 339.48 | 0.1279 | 5.85 | 21.91 |
| 16.35 | 908.20 | 0.1535 | 5.42 | 58.60 |
| 17.77 | 530.91 | 0.1535 | 4.99 | 34.26 |
| 18.83 | 1152.17 | 0.1279 | 4.71 | 74.35 |
| 19.13 | 716.20 | 0.1279 | 4.64 | 46.21 |
| 20.11 | 1549.76 | 0.1279 | 4.41 | 100.00 |
| 20.70 | 779.85 | 0.1279 | 4.29 | 50.32 |
| 21.25 | 852.31 | 0.1791 | 4.18 | 55.00 |
| 22.14 | 470.37 | 0.1791 | 4.02 | 30.35 |
| 23.05 | 979.52 | 0.1535 | 3.86 | 63.20 |
| 24.13 | 760.37 | 0.1791 | 3.69 | 49.06 |
| 25.36 | 655.53 | 0.1535 | 3.51 | 42.30 |
| 25.70 | 390.00 | 0.2047 | 3.47 | 25.17 |
| 26.54 | 210.48 | 0.1535 | 3.36 | 13.58 |
| 27.36 | 129.54 | 0.1535 | 3.26 | 8.36 |
| 28.10 | 348.22 | 0.1535 | 3.18 | 22.47 |
| 32.93 | 38.79 | 0.6140 | 2.72 | 2.50 |
| 34.62 | 198.23 | 0.2047 | 2.59 | 12.79 |
| 37.20 | 63.13 | 0.3070 | 2.42 | 4.07 |
| 38.32 | 112.40 | 0.3070 | 2.35 | 7.25 |

5.1.2 Alternative Preparation Methods

A mixture of free form of Compound II and Tris (molar ratio 1:0.95) in THF/MTBE (1:4, v:v) was stirred for 7 days, followed by vacuum drying at RT for ~3 hours to obtain 1:1 Compound II Tris Salt (Form B) .

EXAMPLE 6

Preparations and Characterization of Crystalline Form of 1:1 Compound II Tris Salt (Form G)

6.1 Preparation Method 15 mg of 1:1 Compound II Tris Salt (Form B) was dissolved in 0.1 mL NMP to form a clear solution. $CH_3CN$ was added to the solution drop by drop. Precipitation was observed. The solids were isolated via centrifugation, heated to 105° C. and then cooled to RT to obtain 1:1 Compound II Tris Salt (Form G).

Figure 8:
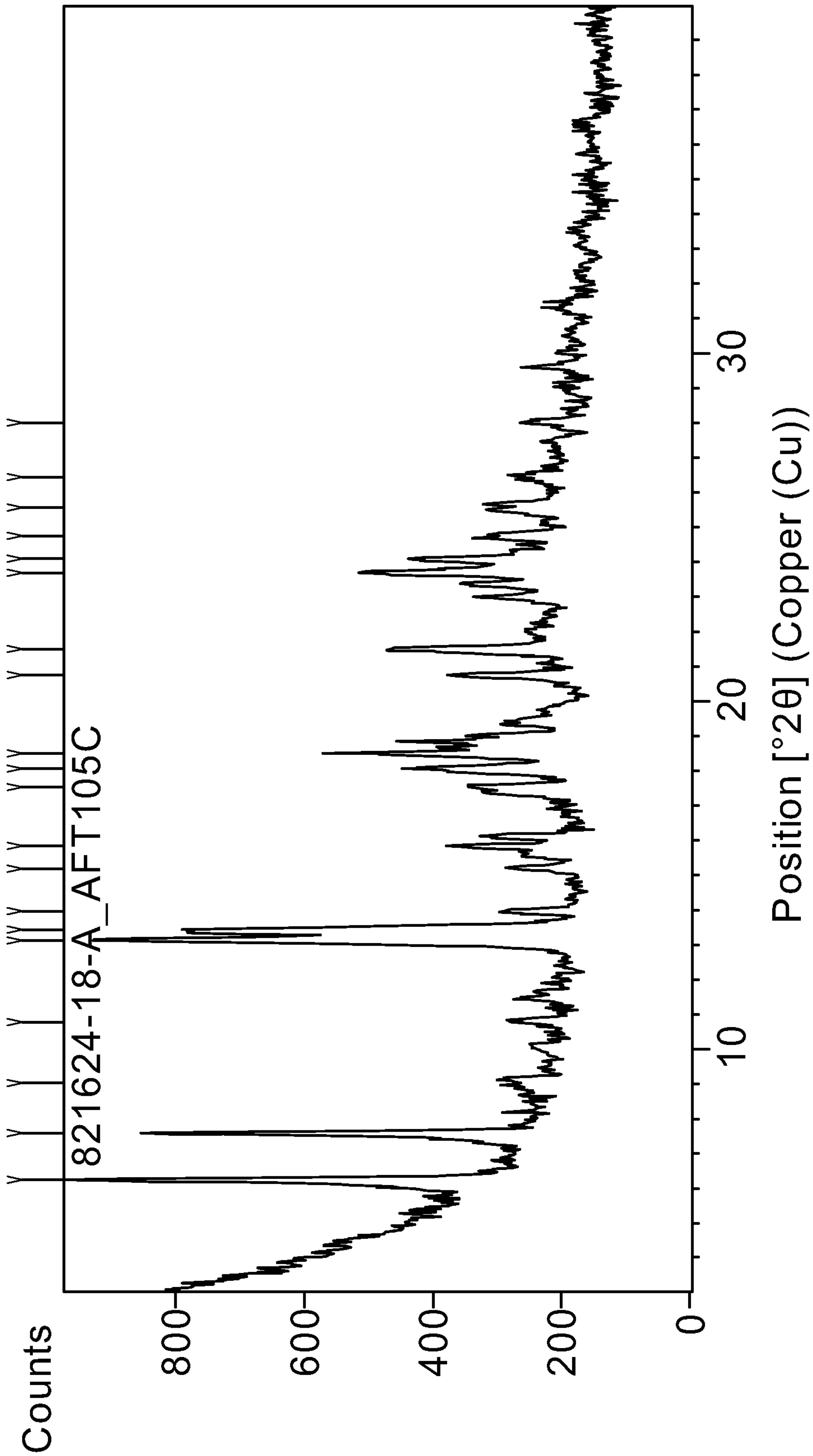
FIG. 8 shows the X-ray Powder Diffraction (XRPD) pattern of 1:1 Compound II Tris Salt (Form G).

The solid obtained was further characterized by XRPD (FIG. 8 and Table 6-1).

Figure 9:
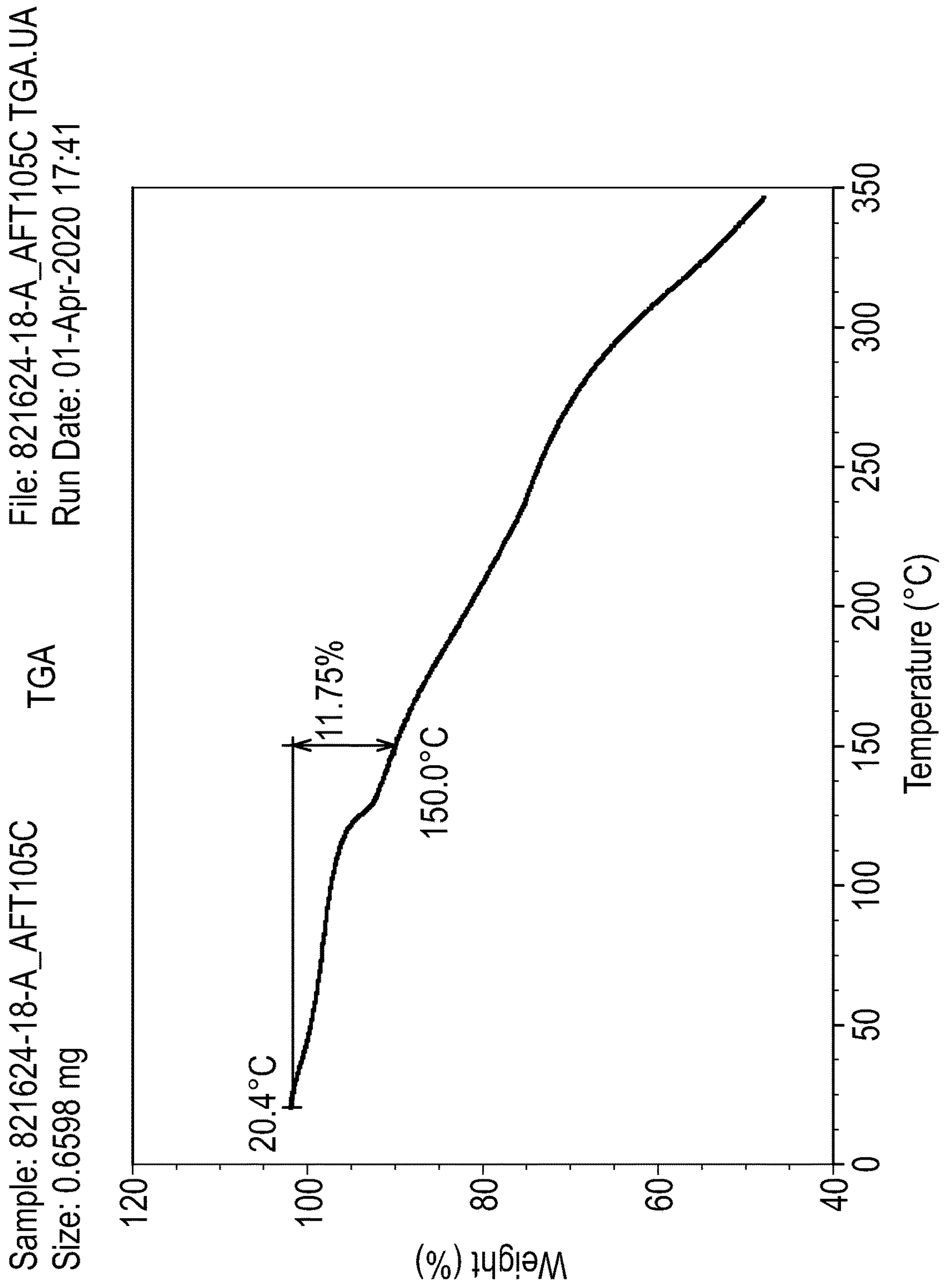
FIG. 9 shows the Thermogravimetric Analysis (TGA) thermogram of 1:1 Compound II Tris Salt (Form G).

The TGA results (FIG. 9) showed a weight loss of 11.75% up to 150° C.

Figure 10:
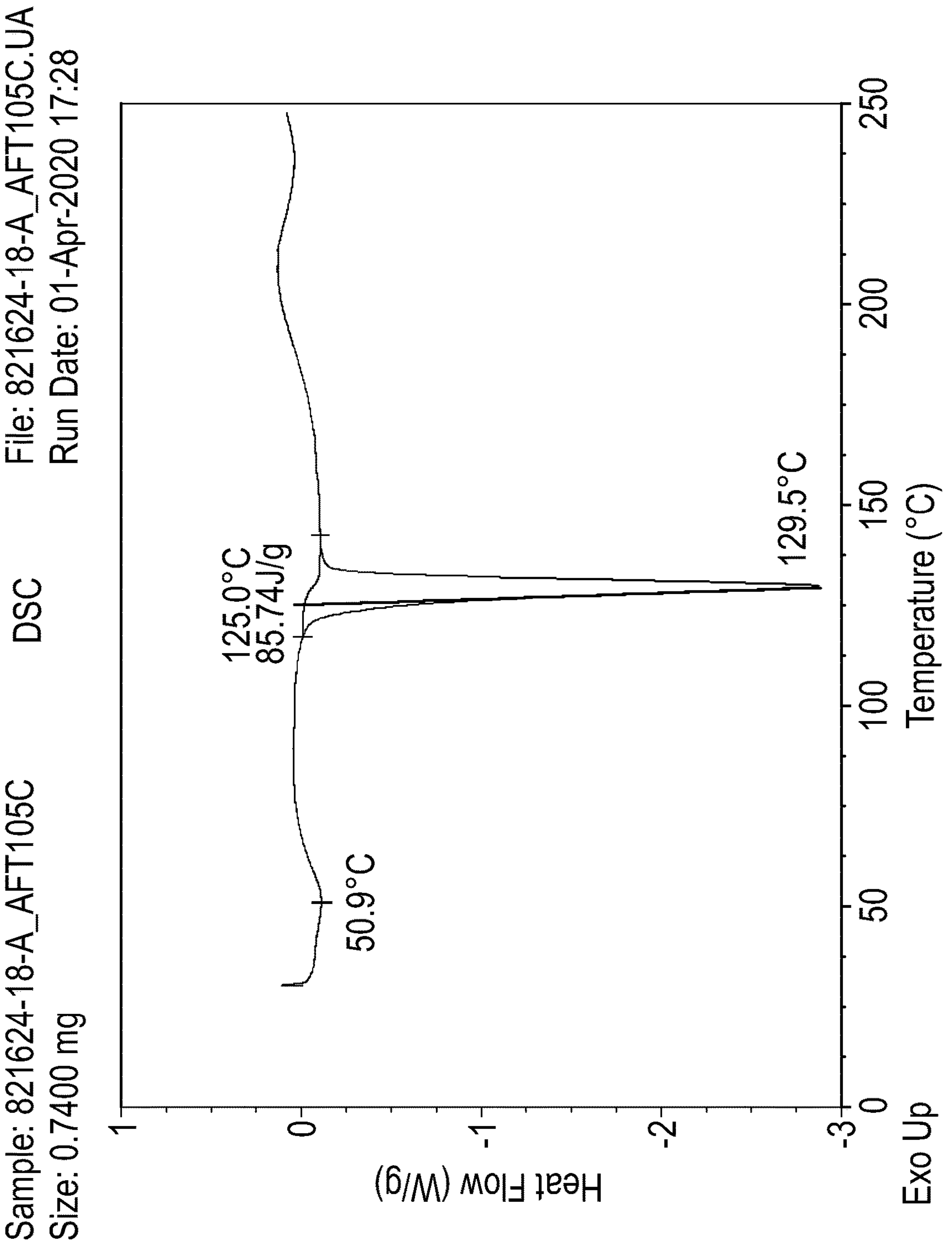
FIG. 10 shows the Differential Scanning calorimetry Analysis (DSC) thermogram of 1:1 Compound II Tris Salt (Form G).

The DSC results (FIG. 10) showed two endotherms at 50.9° C. and 129.5° C. (peak temperature).

TABLE 6-1

XRPD of 1:1 Compound II Tris Salt (Form G)

| Pos. [°2θ] | Height [cts] | FWHM Left [°2θ] | d-spacing [Å] | Rel. Int. [%] |
|---|---|---|---|---|
| 6.24 | 638.21 | 0.1023 | 14.17 | 85.91 |
| 7.58 | 596.40 | 0.1279 | 11.66 | 80.29 |
| 9.01 | 54.20 | 0.3070 | 9.81 | 7.30 |
| 10.77 | 59.75 | 0.3070 | 8.22 | 8.04 |
| 13.13 | 742.85 | 0.1279 | 6.74 | 100.00 |
| 13.44 | 601.18 | 0.1535 | 6.59 | 80.93 |
| 13.96 | 108.40 | 0.1535 | 6.35 | 14.59 |
| 15.19 | 98.84 | 0.1535 | 5.83 | 13.31 |
| 15.83 | 200.56 | 0.1023 | 5.60 | 27.00 |
| 17.54 | 167.99 | 0.3582 | 5.06 | 22.61 |
| 18.04 | 244.06 | 0.2047 | 4.92 | 32.85 |
| 18.50 | 386.27 | 0.0768 | 4.80 | 52.00 |
| 20.75 | 201.38 | 0.1535 | 4.28 | 27.11 |
| 21.50 | 288.94 | 0.1791 | 4.13 | 38.90 |

TABLE 6-1-continued

XRPD of 1:1 Compound II Tris Salt (Form G)

| Pos. [°2θ] | Height [cts] | FWHM Left [°2θ] | d-spacing [Å] | Rel. Int. [%] |
|---|---|---|---|---|
| 23.70 | 336.86 | 0.1535 | 3.75 | 45.35 |
| 24.09 | 263.98 | 0.1535 | 3.69 | 35.54 |
| 24.74 | 135.18 | 0.2047 | 3.60 | 18.20 |
| 25.57 | 126.72 | 0.3070 | 3.48 | 17.06 |
| 26.44 | 90.15 | 0.3070 | 3.37 | 12.14 |
| 28.01 | 66.26 | 0.3070 | 3.19 | 8.92 |

EXAMPLE 7

Characterization of Crystalline Form of 1:1 Compound II Tris Salt (Form B) and 1:1 Compound II Citrate Salt (Form A)

1:1 Compound II Tris Salt (Form B) and 1:1 Compound II Citrate Salt (Form A) were evaluated by kinetic solubility, solid stability and solution stability. Freeform Compound II was also evaluated for comparison. Furthermore, the hygroscopicity of both salts was evaluated by DVS.

7.1 Kinetic Solubility

Kinetic solubility was evaluated for 1:1 Compound II Citrate Salt (Form A), 1:1 Compound II Tris Salt (Form B), and freeform of Compound II in water and three bio-relevant media (SGF, FaSSIF and FeSSIF) for 1/4/24 hours. 3-4 mg of solids were suspended in 3 mL each medium (solid loading:

1 mg/mL, calculated using freeform) to get a suspension, followed by rolling (25 rpm) at 37° C. for 1/4/24 hours. At each time point, ~1.0 mL of suspension was sampled out for centrifugation (12000 rpm, 2 min) and filtration through 0.45 μm PTFE membrane to obtain supernatant for HPLC and pH tests, the residual solids were analyzed by XRPD. Detailed results were summarized in Table 7-1. Based on the results of solubility evaluation, 1:1 Compound II Citrate Salt (Form A) and 1:1 Compound II Tris Salt (Form B) showed similar solubility profile in SGF, FaSSIF and FeSSIF, which was higher than that of freeform within 1 hour. 1:1 Compound II Tris Salt (Form B) showed better solubility in $H_2O$. The purity results were for reference only since the samples were all suspensions.

TABLE 7-1

Summary of kinetic solubility test

| | | 1 hour* | | | | 4 hours* | | | | 24 hours# | | | |
|---|---|---|---|---|---|---|---|---|---|---|---|---|---|
| Material | Media | S | pH | FC | Purity (%)^ | S | pH | FC | Purity (%)^ | S | pH | FC | Purity (%)^ |
| Citrate | $H_2O$ | 0.02 | 4.8 | No | 100.00 | 0.02 | 4.2 | No | 91.26 | 0.05 | 3.4 | No | 86.05 |
| salt | FaSSIF | 0.1 | 6.3 | No | 94.86 | 0.02 | 6.3 | No | 76.06 | 0.009 | 6.0 | Yes | 61.96 |
| Form A | FeSSIF | 0.2 | 5.0 | No | 98.94 | 0.3 | 5.0 | NA | 95.25 | 0.09 | 4.9 | Yes | 79.88 |
| | SGF | 0.5 | 1.9 | Yes | 96.79 | 0.08 | 1.9 | Yes | 91.83 | 0.06 | 1.9 | Yes | 90.59 |
| Tris | $H_2O$ | 0.4 | 7.6 | No | 93.07 | 0.9 | 7.8 | Yes | 93.13 | 0.6 | 7.9 | Yes | 92.03 |
| salt | FaSSIF | 0.07 | 6.6 | NA | 72.58 | 0.05 | 6.6 | Yes | 59.86 | 0.1 | 6.5 | Yes | 72.13 |
| Form B | FeSSIF | 0.2 | 5.1 | No | 98.18 | 0.3 | 5.1 | Yes | 93.37 | 0.3 | 5.0 | Yes | 80.52 |
| | SGF | 0.6 | 1.9 | Yes | 93.44 | 0.2 | 2.0 | Yes | 84.69 | 0.2 | 2.0 | Yes | 82.04 |
| Freeform | $H_2O$ | 0.03 | 6.6 | No | 93.84 | 0.03 | 7.0 | No | 86.44 | 0.04 | 7.3 | No | 89.76 |
| | FaSSIF | 0.02 | 6.5 | No | 85.92 | 0.02 | 6.5 | No | 72.84 | 0.02 | 6.4 | Yes | 66.76 |

TABLE 7-1-continued

| Summary of kinetic solubility test | | | | | | | | | | | | | |
|---|---|---|---|---|---|---|---|---|---|---|---|---|---|
| | | 1 hour* | | | | 4 hours* | | | | 24 hours# | | | |
| Material | Media | S | pH | FC | Purity (%)^ | S | pH | FC | Purity (%)^ | S | pH | FC | Purity (%)^ |
| | FeSSIF | 0.03 | 5.0 | No | 71.16 | 0.02 | 5.1 | Yes | 47.29 | 0.04 | 5.0 | No | 37.65 |
| | SGF | 0.2 | 1.9 | No | 94.17 | 0.2 | 1.9 | Yes | 81.32 | 0.1 | 1.8 | Yes | 76.04 |

S: solubility (mg/mL).
FC: form change.
^Area percentage of API (calculated by area normalization method). The data was for reference only since the samples were suspensions.
*LOQ = 0.38 μg/mL, HOQ = 176.8 μg/mL;
#LOQ = 0.16 μg/mL, HOQ = 176.8 μg/mL;
NA: The sample was insufficient for XRPD test.

7.2.1 Solid Stability Evaluation (I/II)

To evaluate the physical and chemical stability of 1:1 Compound II Citrate Salt (Form A), 1:1 Compound II Tris Salt (Form B) and freeform, samples were stored under the conditions of 60° C. for 1 day and 25° C./60% RH or 40° C./75% RH for 1 week, respectively. The solids were characterized using XRPD and HPLC, and the results were summarized in Table 7-2-1. As evidenced by XRPD results and HPLC chromatograms, no form change was observed after one week. 1:1 Compound II Citrate Salt (Form A) and 1:1 Compound II Tris Salt (Form B) showed better chemical stability than freeform of Compound II.

TABLE 7-2-1

| Summary of solid stability evaluation (I/II) | | | | | |
|---|---|---|---|---|---|
| Starting material | Experimental condition | Sampling time | Observation | Form change | Purity* (area %) |
| Citrate salt Form A | Initial | — | White powder | No | 97.73 |
| | 60° C. (capped) | 1 day | White powder | No | 97.50 |
| | 25° C./60% RH (open) | 1 week | White powder | No | 97.58 |
| | 40° C./75% RH (open) | 1 week | White powder | No | 97.14 |
| Tris salt Form B | Initial | — | Yellowish powder | No | 94.56 |
| | 60° C. (capped) | 1 day | Yellow powder | No | 92.98 |
| | 25° C./60% RH (open) | 1 week | Yellow powder | No | 93.86 |
| | 40° C./75% RH (open) | 1 week | Yellow powder | No | 94.13 |
| Freeform | Initial | — | Yellow powder | No | 95.27 |
| | 60° C. (capped) | 1 day | Yellow powder | No | 88.94 |
| | 25° C./60% RH (open) | 1 week | Yellow powder | No | 94.58 |
| | 40° C./75% RH (open) | 1 week | Yellow powder | No | 92.86 |

*Area percentage of API (calculated with area normalization method).

7.2.2 Solid Stability Evaluation (II/II)

The chemical stability of 1:1 Compound II Citrate Salt (Form A) and 1:1 Compound II Tris Salt (Form B) was further evaluated at solid state, samples were stored under the ambient condition or 40° C./75% RH for 1 day and 3 days, respectively. The HPLC purity and weight purity were tested using HPLC in triplicate, and the results were summarized in Table 7-2-2. 1:1 Compound II Citrate Salt (Form A) and 1:1 Compound II Tris Salt (Form B) showed similar chemical stability in the evaluated conditions.

TABLE 7-2-2

| Summary of solid stability evaluation (II/II) | | | | | |
|---|---|---|---|---|---|
| Material | Experimental condition | Sampling ID | Sampling time | Ave. Purity* (area %) | CV** (%) |
| Citrate salt Form A | Initial | A1 | — | 97.9 | 0.2 |
| | Ambient condition (open) | A2 | 1 day | 97.8 | 0.1 |
| | | A3 | 3 days | 97.8 | 0.6 |
| | 40° C./75% RH (open) | C2 | 1 day | 97.8 | 0.4 |
| | | C3 | 3 days | 97.9 | 0.3 |
| Tris salt Form B | Initial | B1 | — | 95.5 | 0.2 |
| | Ambient condition (open) | B2 | 1 day | 94.4 | 0.5 |
| | | B3 | 3 days | 94.2 | 0.1 |
| | 40° C./75% RH (open) | D2 | 1 day | 94.5 | 0.1 |
| | | D3 | 3 days | 94.8 | 0.2 |

*Tested using HPLC in triplicate, calculated by average.
**CV: Coefficient of variation.

7.3 Solution Stability Evaluation

Solution stability was evaluated for 1:1 Compound II Citrate Salt (Form A) and 1:1 Compound II Tris Salt (Form B) in SGF (pH 1.8) and pH 8.0 buffer at RT. Clear solutions were prepared at two concentrations (0.01 mg/mL, 0.05 mg/mL) and then placed at RT for 6 hours, 1/5 days or 6 hours, 1/3/7 days. Both salts showed better stability in pH 8.0 buffer, while the purity of the pH 1.8 solution decreased slightly after 1 day. The HPLC purity and pH value were tested and the results were summarized from Table 7-3-1 to Table 7-3-4.

TABLE 7-3-1

| Summary of solution stability evaluation for Citrate Salt (Form A) (I/II) | | | | | | |
|---|---|---|---|---|---|---|
| | | Initial | | 6 hours | | |
| Concentration | Media | Purity (% area) | pH | Purity (% area) | Purity vs. Initial(%) | pH |
| 0.01 mg/mL | pH 1.8 | 100.00 | 1.8 | 100.00 | 100.0 | 1.8 |
| 0.05 mg/mL | (SGF) | 97.84 | 1.8 | 97.54 | 99.7 | 1.8 |
| 0.01 mg/mL | pH 8.0 | 98.67 | 8.0 | 97.89 | 99.2 | 8.0 |
| 0.05 mg/mL | (50 mM phosphate) | 98.22 | 8.0 | 98.03 | 99.8 | 8.0 |

TABLE 7-3-2

| Summary of solution stability evaluation for Citrate Salt (Form A) (II/II) | | | | | | | |
|---|---|---|---|---|---|---|---|
| | | 1 day | | | 5 days | | |
| Concentration | Media | Purity (% area) | Purity vs. Initial (%) | pH | Purity (% area) | Purity vs. Initial (%) | pH |
| 0.01 mg/mL | pH 1.8 | 98.51 | 98.5 | 1.8 | 94.05 | 94.1 | 1.9 |
| 0.05 mg/mL* | (SGF) | 96.61 | 98.7 | 1.8 | 92.31 | 96.1 | 1.8 |
| 0.01 mg/mL | pH 8.0 | 97.36 | 98.7 | 8.0 | 97.14 | 98.5 | 7.9 |
| 0.05 mg/mL | (50 mM phosphate) | 97.95 | 99.7 | 8.0 | 97.75 | 99.5 | 8.0 |

*The sample turned turbid after 5 days.

TABLE 7-3-3

| Summary of solution stability evaluation for Tris Salt (Form B) (I/II) | | | | | | | | | | |
|---|---|---|---|---|---|---|---|---|---|---|
| | | Initial | | 6 hours | | | 1 day | | | |
| Concentration | Media | Purity (% area) | pH | Purity (% area) | Purity vs. Initial(%) | pH | Purity (% area) | Purity vs. Initial(%) | pH |
| 0.01 mg/mL | pH 1.8 | 95.25 | 1.8 | 94.92 | 99.7 | 1.8 | 94.11 | 98.8 | 1.8 |
| 0.05 mg/mL | (SGF) | 98.26 | 1.8 | 97.53 | 99.3 | 1.8 | 96.40 | 98.1 | 1.8 |
| 0.01 mg/mL | pH 8.0 | 99.04 | 8.0 | 98.97 | 99.9 | 8.0 | 98.38 | 99.3 | 8.0 |
| 0.05 mg/mL | (50 mM phosphate) | 99.27 | 8.0 | 99.28 | 100.0 | 8.0 | 98.86 | 99.6 | 8.0 |

TABLE 7-3-4

| Summary of solution stability evaluation for Tris Salt (Form B) (II/II) | | | | | | | |
|---|---|---|---|---|---|---|---|
| | | 3 days | | | 7 days | | |
| Concentration | Media | Purity (% area) | Purity vs. Initial (%) | pH | Purity (% area) | Purity vs. Initial (%) | pH |
| 0.01 mg/mL | pH 1.8 | 91.81 | 96.4 | 1.8 | 87.14 | 91.5 | 1.8 |
| 0.05 mg/mL* | (SGF) | 93.38 | 95.0 | 1.8 | 87.15* | 88.7 | 1.8 |
| 0.01 mg/mL | pH 8.0 | 98.26 | 99.2 | 8.0 | 97.31 | 98.3 | 8.0 |
| 0.05 mg/mL | (50 mM phosphate) | 98.98 | 99.7 | 8.0 | 98.75 | 99.5 | 8.0 |

*The sample turned turbid after 7 days.

7.4 Hygroscopicity

To investigate the solid form stability as a function of humidity, DVS isotherm plots of 1:1 Compound II Citrate Salt (Form A) and 1:1 Compound II Tris Salt (Form B) were collected at 25° C. between 0% RH and 95% RH. The results were summarized in Table 7-4. For 1:1 Compound II Citrate Salt (Form A), a water uptake of 0.71% was observed at 25° C./80%RH. For 1:1 Compound II Tris Salt (Form B), the water uptake increased by 2.47% between 0% and 10% RH on the cycle 2 sorption curve. The water uptake increased by 0.97% from 10% to 80% RH and a platform was observed. No form change was observed for both salts after DVS test.

TABLE 7-4

| Summary of DVS test | | | |
|---|---|---|---|
| Salt | Water uptake (25° C./80% RH) | Hygroscopicity[2] | Form change |
| Citrate salt Form A | 0.71% | Slightly hygroscopic | No |
| Tris salt Form B | 0.97%* | Slightly hygroscopic | No |

*Water uptake from 10% RH to 80% RH.

What is claimed is:

1. A tris salt of Compound I, wherein Compound I is represented by the following structural formula:

Compound I

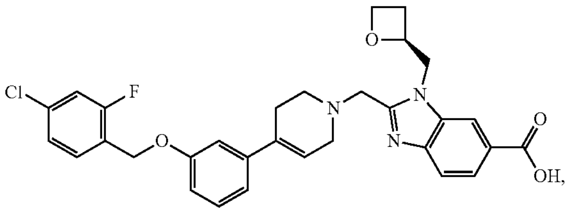

wherein the molar ratio between Compound I and tris (hydroxymethyl)aminomethane is 1:1.

2. The tris salt of claim 1, wherein the tris salt is a monohydrate.

3. The tris salt of claim 1, wherein the tris salt is in a single crystalline form, Form A, characterized by an X-ray powder diffraction pattern which comprises at least three peaks selected from 17.5°, 20.1°, 20.7°, 21.1°, and 22.6°±0.2 in 2θ.

4. The tris salt of claim 3, wherein the tris salt is in a single crystalline form, Form A, characterized by a differential scanning calorimeter (DSC) peak phase transition temperature of 173±3° C.

5. The tris salt of claim 4, wherein at least 90% by weight of the tris salt is in single crystalline Form A.

6. A pharmaceutical composition comprising the compound of claim 1, and a pharmaceutically acceptable carrier.

7. A method of treating cardiometabolic and associated diseases, the method comprising administering to a subject in need of such treatment a therapeutically effective amount of a salt of claim 1, or a pharmaceutical composition thereof, wherein the disease is type 1 diabetes (TID), type 2 diabetes mellitus (T2DM), hyperglycemia, kidney disease, obesity, nonalcoholic fatty liver disease (NAFLD), nonalcoholic steatohepatitis (NASH), cardiovascular disease, hypertension, Parkinson's Disease, and Alzheimer's Disease.

8. The tris salt of claim 2, wherein the tris salt is in a single crystalline form, Form A, characterized by an X-ray powder diffraction pattern which comprises peaks at 17.5°, 20.1°, 20.7°, 21.1°, and 22.6°±0.2 in 2θ.

9. The tris salt of claim 2, wherein the tris salt is in a single crystalline form, Form A, characterized by an X-ray powder diffraction pattern which comprises peaks at 4.1°, 14.8°, 17.5°, 18.8°, 20.1°, 20.7°, 21.1°, and 22.6°±0.2 in 2θ.

10. The tris salt of claim 2, wherein the tris salt is in a single crystalline form, Form A, characterized by an X-ray powder diffraction pattern which comprises peaks at 4.1°, 8.1°, 12.8°, 14.8°, 16.3°, 17.5°, 18.8°, 19.3°, 20.1°, 20.7°, 21.1°, 22.6°, 25.1°, and 25.8°±0.2 in 2θ.

11. The tris salt of claim 1, wherein the tris salt is unsolvated.

12. The method of claim 7, wherein the disease is type 2 diabetes mellitus.

13. The method of claim 7, wherein the disease is obesity.

14. The method of claim 7, wherein the disease is Alzheimer's Disease.

15. The method of claim 7, wherein the disease is Parkinson's Disease.

16. The method of claim 7, wherein the disease is hyperglycemia.

17. The method of claim 7, wherein the disease is nonalcoholic fatty liver disease.

18. The method of claim 7, wherein the disease is nonalcoholic steatohepatitis.

19. The method of claim 7, wherein the disease is type 1 diabetes.

20. The method of claim 7, wherein the disease is cardiovascular disease.

21. The method of claim 7, wherein the disease is hypertension.

22. The method of claim 7, wherein the disease is kidney disease.

* * * * *